(12) United States Patent
Jones et al.

(10) Patent No.: US 9,901,462 B2
(45) Date of Patent: Feb. 27, 2018

(54) FEMORAL COMPONENT INSTRUMENT

(71) Applicant: Zimmer, Inc., Warsaw, IN (US)

(72) Inventors: Nolan C. Jones, Warsaw, IN (US); Jeffery A. VanDiepenbos, Syracuse, IN (US)

(73) Assignee: Zimmer, Inc., Warsaw, IN (US)

( * ) Notice: Subject to any disclaimer, the term of this patent is extended or adjusted under 35 U.S.C. 154(b) by 0 days.

(21) Appl. No.: 14/943,280

(22) Filed: Nov. 17, 2015

(65) Prior Publication Data
US 2016/0067057 A1 Mar. 10, 2016

Related U.S. Application Data

(63) Continuation of application No. 13/181,070, filed on Jul. 12, 2011, now Pat. No. 9,220,611.

(51) Int. Cl.
*A61F 2/00* (2006.01)
*A61F 2/46* (2006.01)
(Continued)

(52) U.S. Cl.
CPC ............ *A61F 2/4607* (2013.01); *A61B 17/92* (2013.01); *A61F 2/4603* (2013.01); *A61F 2/3859* (2013.01);
(Continued)

(58) Field of Classification Search
CPC .............. A61F 2/461; A61F 2002/4623; A61F 2002/4624; A61F 2002/4625; A61F 2002/4681
(Continued)

(56) References Cited

U.S. PATENT DOCUMENTS 4,364,389 A 12/1982 Keller
4,889,022 A 12/1989 Peviani
(Continued)

FOREIGN PATENT DOCUMENTS

GB 2307861 A 6/1997

OTHER PUBLICATIONS

"U.S. Appl. No. 13/181,070, Advisory Action dated Sep. 25, 2014", 2 pgs.
(Continued)

*Primary Examiner* — Matthew Lawson
(74) *Attorney, Agent, or Firm* — Schwegman Lundberg & Woessner, P.A.

(57) ABSTRACT

A femoral component instrument includes a rotatable locking mechanism such as a post and is capable of interchangeable use between posterior stabilizing ("PS") and cruciate retaining ("CR") femoral component types via the locking mechanism. The instrument further includes a modular pad so that a pad specific to the prosthesis type may be chosen. Each pad of a particular femoral component type is useable with a variety of sizes of that femoral component type. The locking mechanism of the instrument is alternatively useable with a variety of femoral component types. The locking end of the post keys to a pad aperture to rotatably align the post to an appropriate securement position. If a femoral component is not locked to the pad, the post of the instrument moves from an exposed position proximal to the proximal pad surface to a retracted position distal to the proximal pad surface, thereby permitting impaction.

16 Claims, 14 Drawing Sheets

(51) Int. Cl.
*A61B 17/92* (2006.01)
*A61F 2/38* (2006.01)

(52) U.S. Cl.
CPC ....... *A61F 2/461* (2013.01); *A61F 2002/4622* (2013.01); *A61F 2002/4627* (2013.01); *A61F 2002/4628* (2013.01)

(58) Field of Classification Search
USPC .............................. 606/86 R, 88, 89, 99, 100
See application file for complete search history.

(56) References Cited

U.S. PATENT DOCUMENTS

| | | | |
|---|---|---|---|
| 4,919,679 A | 4/1990 | Averill | |
| 5,059,196 A | 10/1991 | Coates | |
| 5,064,427 A | 11/1991 | Burkinshaw | |
| 5,333,773 A | 8/1994 | Main et al. | |
| 5,356,414 A | 10/1994 | Cohen et al. | |
| 5,409,492 A | 4/1995 | Jones et al. | |
| 5,514,136 A | 5/1996 | Richelsoph | |
| 5,733,292 A | 3/1998 | Gustilo et al. | |
| 5,788,701 A | 8/1998 | Mccue | |
| 5,849,015 A | 12/1998 | Haywood et al. | |
| 6,113,605 A | 9/2000 | Storer | |
| 6,783,551 B1 | 8/2004 | Metzger et al. | |
| 7,048,742 B2 | 5/2006 | Keller | |
| 7,338,497 B2 | 3/2008 | Coon et al. | |
| 7,776,044 B2 | 8/2010 | Pendleton et al. | |
| 8,435,241 B2 | 5/2013 | Correia et al. | |
| 8,758,360 B2 | 6/2014 | Green, II | |
| 8,870,886 B2 | 10/2014 | Burgi | |
| 8,986,390 B2 | 3/2015 | Wogoman et al. | |
| 9,095,356 B2 | 8/2015 | Thomas et al. | |
| 9,107,757 B2 | 8/2015 | Major et al. | |
| 9,220,611 B2 | 12/2015 | Jones et al. | |
| 2001/0034554 A1 | 10/2001 | Pappas | |
| 2002/0092871 A1* | 7/2002 | Rickard | B05C 17/01 222/327 |
| 2004/0010261 A1 | 1/2004 | Hoag et al. | |
| 2005/0124998 A1 | 6/2005 | Coon et al. | |
| 2006/0095043 A1* | 5/2006 | Martz | A61B 17/1671 606/90 |
| 2006/0136067 A1 | 6/2006 | Pendleton et al. | |
| 2006/0200162 A1* | 9/2006 | Farling | A61B 17/155 606/88 |
| 2007/0167952 A1* | 7/2007 | Burgi | A61B 17/162 606/99 |
| 2008/0119941 A1 | 5/2008 | Seo et al. | |
| 2009/0036909 A1 | 2/2009 | Perry et al. | |
| 2011/0186456 A1 | 8/2011 | Bertazzoni et al. | |
| 2012/0143204 A1 | 6/2012 | Blaylock et al. | |
| 2013/0018382 A1 | 1/2013 | Jones et al. | |
| 2014/0094812 A1 | 4/2014 | Edwards et al. | |
| 2014/0277541 A1 | 9/2014 | Wyss et al. | |
| 2015/0045800 A1 | 2/2015 | Berelsman et al. | |
| 2015/0342742 A1 | 12/2015 | Ferro et al. | |

OTHER PUBLICATIONS

"U.S. Appl. No. 13/181,070, Examiner Interview Summary dated Jun. 17, 2015", 3 pgs.
"U.S. Appl. No. 13/181,070, Final Office Action dated Jun. 26, 2014", 18 pgs.
"U.S. Appl. No. 13/181,070, Non Final Office Action dated Apr. 20, 2015", 16 pgs.
"U.S. Appl. No. 13/181,070, Non Final Office Action dated Nov. 26, 2013", 19 pgs.
"U.S. Appl. No. 13/181,070, Notice of Allowance dated Aug. 21, 2015", 5 pgs.
"U.S. Appl. No. 13/181,070, Response filed May 27, 2014 to Non-Final Office Action dated Nov. 26, 2013", 18 pgs.
"U.S. Appl. No. 13/181,070, Response filed Jul. 17, 2015 to Non Final Office Action dated Apr. 20, 2015", 14 pgs.
"U.S. Appl. No. 13/181,070, Response filed Sep. 19, 2014 to Final Office Action dated Jun. 26, 2014", 16 pgs.
"U.S. Appl. No. 13/181,070, Response filed Oct. 22, 2013 to Restriction Requirement dated Sep. 23, 2013", 13 pgs.
"U.S. Appl. No. 13/181,070, Restriction Requirement dated Sep. 23, 2013", 5 pgs.
"Journey BCS total knee replacement Part 2, Dr. Venkatachalam, accessed Dec. 15, 2010 and May 28, 2012", This link shows the use of surgical instruments (0:30 starts use of a provisional extractor, 4:00 starts use of an implant inserter), [Online]. Retrieved from the Internet: <http://www.youtube.com/watch?v=zWPIkUbMfZI> on Dec. 16, 2013, (Sep. 21, 2010), 2 pgs.
"Oxinium Knee Replacement—Venkatachalam Part 1, accessed Dec. 15, 2010 and May 28, 2012", This link shows the use of a trial impactor/extractor (starting at 5:15 and continued on the below link), [Online]. Retrieved from the Internet: <http://www.youtube.com/watch?v=J-KFQDB6Tb4&feature=related> on Dec. 16, 2013, (Jul. 27, 2010), 2 pgs.
"Smith & Nephew Journey BCS Bi-Cruciate Stabilized Knee System Surgical Technique", Smith—Nephew, Inc. Sep. 2007, 1-60.
"Zimmer MIS Intramedullary Instrumentation Surgical Technique for NexGen Cruciate Retaining & NexGen Legacy Posterior Stabilized Knees", printed 2005, 2009, Zimmer, Inc., (2009), 45 pgs.

* cited by examiner

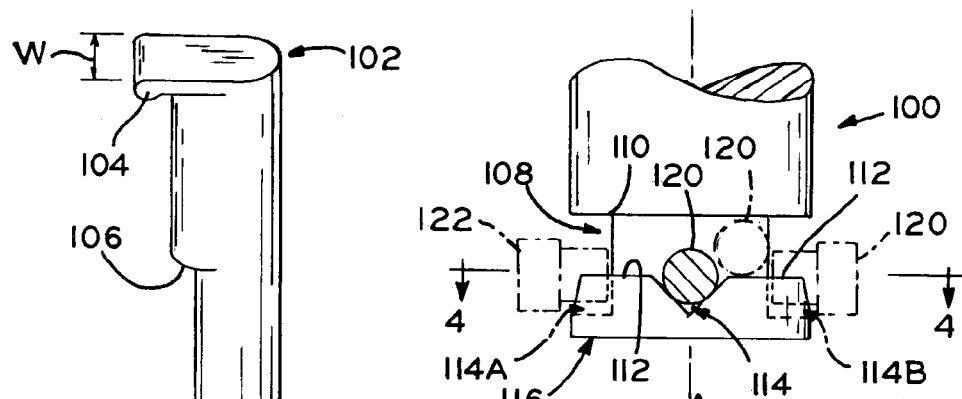
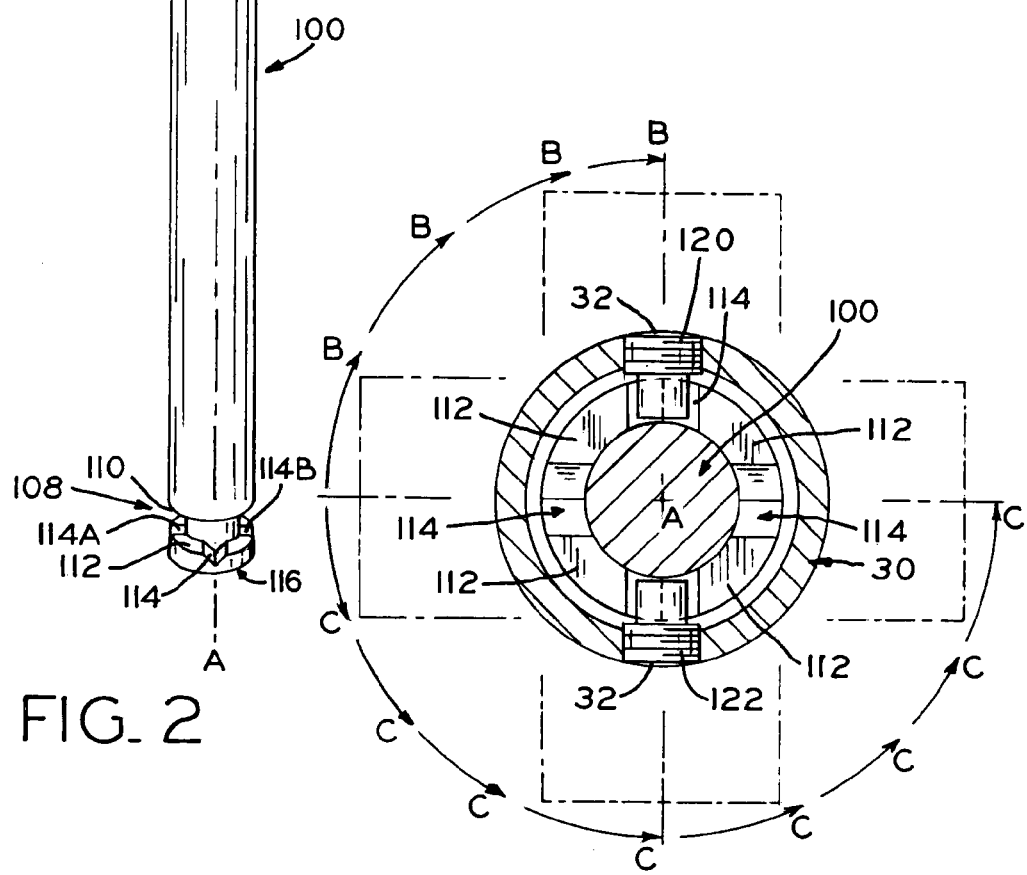

FIG_10

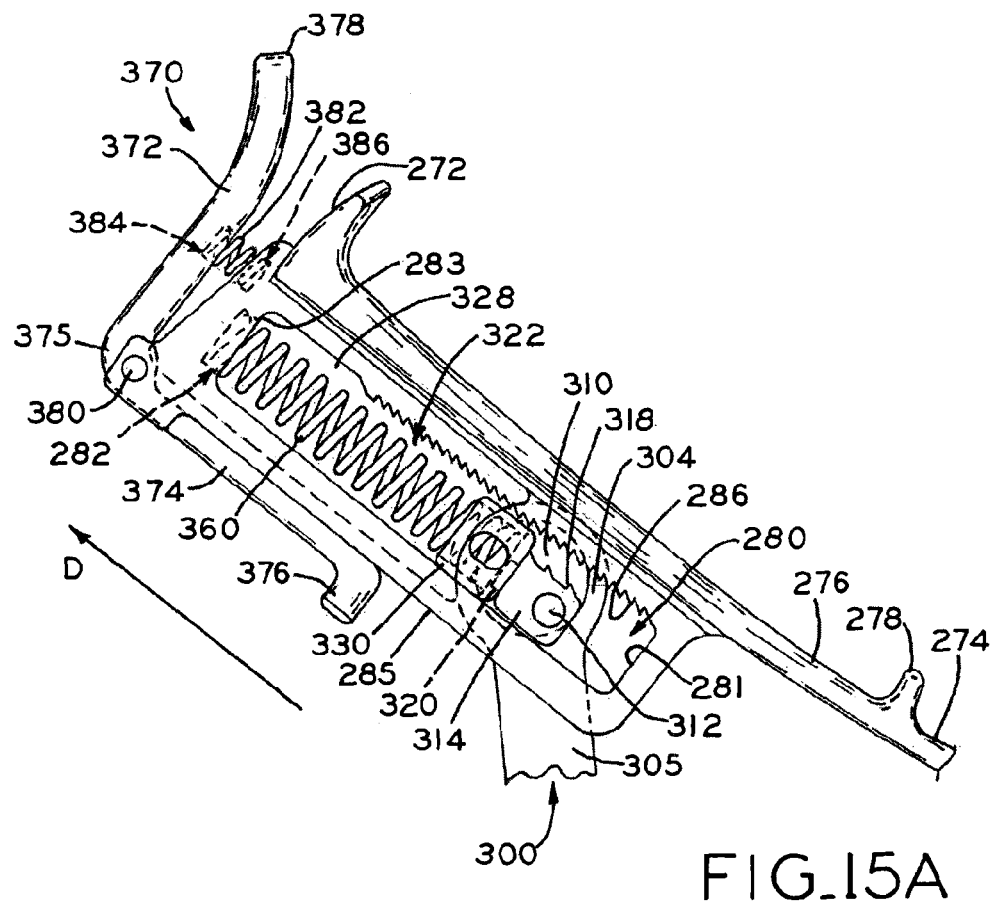
FIG_15A
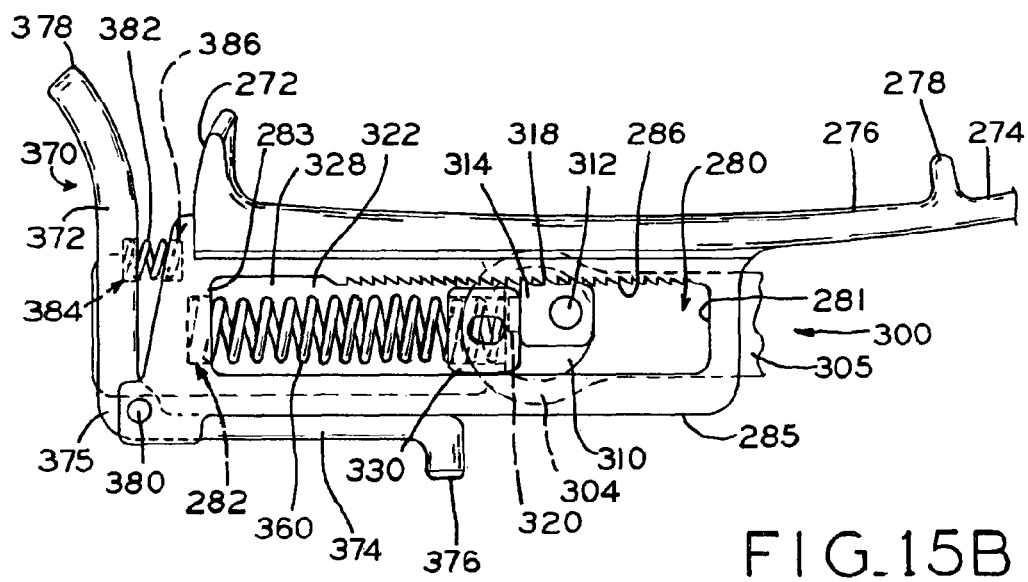
FIG_15B

FEMORAL COMPONENT INSTRUMENT

BACKGROUND

1. Field of Disclosure

The present disclosure relates to instruments used in orthopedic surgery, and, in particular, to a femoral component instrument, which can be used as an inserter, impactor and extractor for use in the placement, impaction and extraction of a femoral prosthesis or femoral provisional component, for example.

2. Description of Related Art

The knee is the joint between the femur and the tibia. The knee joint is formed of a pair of condyles located at a distal portion of the femur, a tibial plateau located at a proximal end of the tibia and shaped to mate with the pair of condyles, and a pair of menisci positioned between the tibial plateau and the condyles. A knee may incur wear, significant disease, or trauma that warrants replacement of the knee with a prosthetic knee implant including prosthetic components such as a femoral component to replace the distal end of the femur, a tibial component to replace the proximal end of the tibia, and a bearing insert to replace articulating tissue between the femur and the tibia. The condyles of the prosthetic femoral component will have a shape corresponding to the shape of the natural condyles of the distal femur.

Orthopedic procedures for the replacement of all, or a portion of, a patient's joint typically require reshaping of the bones of the knee joint to receive such prosthetic components. Procedures for implanting a total knee prosthesis involve preparing and reshaping both the distal end of the femur and the proximal end of the tibia prior to implanting the respective prosthetic components. Resection of the femur generally involves making five intersecting generally planar cuts, and resection of the tibial plateau generally involves a single cut. The amount of bone removed is determined, in part, by the size and type of components being implanted.

During a surgical procedure to implant a prosthetic knee joint, a provisional femoral component and a provisional tibial component can be placed on a distal femur and proximal tibia, respectively, after resecting the distal femur and proximal tibia. The provisional components assist with confirming the proper size and position of the permanent femoral and tibial components. The provisional components typically come in a range of sizes representative of the size and shape of the permanent components of the chosen prosthesis system. Provisional components are typically selected after making a preliminary determination of the proper size of the permanent components. A trial reduction of the knee joint with the provisional components in place may indicate that the preliminary size determination was not ideal. Alternative provisional components can then be selected and another trial reduction performed. After determining the proper size components, final prosthesis components are seated. Proper insertion and extraction of the provisional components and subsequent placement of the final prosthesis components requires reliable grasping and manipulation of the provisional and final prosthesis components. Because the inserter of the present disclosure is usable with both provisional and final prosthesis components, "femoral components" will be generically used in this document to denote either a provisional or a final prosthesis component.

An inserter can be utilized to grasp and hold the various femoral components to facilitate placement or removal of the same during the surgical procedure. Femoral component inserters can utilize a pad to contact the condyles of the femoral component in conjunction with an opposing element placed against the bone contacting surface of the femoral component and drawn toward the pad to thereby assert a compressive force against opposing sides of the femoral component to hold the femoral component to the inserter. One such inserter is described in the Zimmer® MIS Intramedullary Instrumentation Surgical Technique for Nex-Gen® Cruciate Retaining and NexGen® Legacy Posterior Stabilized Knees submitted herewith in an Information Disclosure Statement, the entire disclosure of which is hereby explicitly incorporated by reference herein, and in U.S. Patent App. Publ. No. 2006/0200162, entitled "Total Knee Arthroplasty Instruments," the entirety of which is hereby incorporated by reference herein.

A typical knee prosthesis system includes not only a variety of different sized femoral components but also a variety of femoral component types, offering differing levels of constraint. For example, a knee prosthesis system may include a number of sizes of a highly unconstrained knee prosthesis for use in cases where the natural ligaments can be retained to provide stability to the joint. Such prostheses are typically referred to as cruciate retaining ("CR") prostheses. The chosen prosthesis system may also include a number of sizes of a more highly constrained knee prosthesis including one which utilizes a femoral cam and a tibial spine to stabilize and/or guide movement of the prosthetic components relative to each other. Such prostheses are typically referred to as posterior stabilized ("PS") prostheses. CR and PS femoral components typically incorporate different features on their bone contacting sides. For example, PS femoral components can include a box extending proximally from the distal bone contacting surface to accommodate the spine of the corresponding tibial component.

To accommodate alternative insertion of, for example, PS and CR femoral components, alternative inserters, i.e., one particular to the CR implant and one particular to the PS implant may be utilized. During certain surgical procedures, a surgeon may, intraoperatively, decide that a more constrained prosthesis is needed. For example, a surgeon may preoperatively decide that a CR prosthesis is indicated, but during surgery determine that joint physiology requires a more constrained prosthesis such as a PS prosthesis. In such circumstances, a surgeon may alter his choice of both implant and inserter.

After inserting the PS or CR prosthesis onto a prepared distal femur of a patient, a surgeon utilizes an impactor device separate from the inserter to impact the inserted prosthesis against the contacting bone. As securement mechanisms of inserters tend to secure to a bone contacting surface of a prosthesis, utilizing the inserter as an impactor is generally not possible. Owing to the extension of the securement mechanism beyond the prosthesis contacting surface of the inserter, the securement mechanism could interrupt the desired contact between the bone contacting surface of the prosthesis and the bone to be contacted and/or impact portions of the distal femur aligned with the intercondylar notch of the femoral component.

SUMMARY

The present disclosure provides a femoral component inserter including a securement or locking mechanism that provides differing securement locations for PS and CR femoral components. The inserter includes a modular pad so that a pad specific to the prosthesis type (e.g., PS or CR) may be chosen. Each pad of a particular femoral component type is useable with a variety of sizes of that femoral component type. The femoral component inserter of the present disclosure further includes a locking feature which contacts a bone contacting surface of a femoral component to lock the femoral component to the inserter and which can be recessed into the condylar contact pad of the inserter so that the inserter can be used as an impactor, without interference of the locking feature with the femoral component and/or femur during impaction.

In an embodiment of the present disclosure, the locking mechanism includes a rotatable post having a locking lip extending transversely from the post at a locking end for interchangeable engagement with either a PS or a CR femoral component. Rotation of the post and, consequently, the locking lip allows the locking mechanism to be adjusted to accommodate the differing features on the bone contacting surfaces of PS and CR femoral components. Rotation of the post/locking lip combination further allows the locking lip to be aligned relative to the distal most points of the condylar surfaces of the femoral component in question so that the direction of the force provided to the femoral component by the inserter intersects or is spaced a small amount (approximately 3 mm) from a line formed by the distal most points of the medial and lateral condylar surfaces of the femoral component, which yields a highly stable locked configuration between the inserter and the femoral component. In certain configurations, the femoral component contacts the pad at an anterior contact point and a posterior contact point on each condyle, resulting in four contact points and a contact line between each pair of contact points on each condyle. In these configurations, the post/locking lip combination can supply a force in a direction that is substantially equidistant to each contact point on a particular line.

In an embodiment of the present disclosure, the locking lip is rotated 90° from a first position in which it is useable to secure the inserter to a CR femoral component to a second position in which it is useable to secure the inserter to a PS femoral component. A locking end of the post from which the locking lip extends is keyed to an aperture in either a CR or PS pad such that the locking lip must be positioned in a securement position appropriate to the prosthesis type particular to the chosen pad when the pad is operably assembled to the inserter.

Further, the inserter may act as an impactor when a femoral component is not locked to the pad. In that instance, the post of the inserter from which the locking lip extends is capable of movement from an external, exposed position extending outwardly from the condylar contact surface of the pad to an internal, retracted position in which the post does not extend from the condylar contact surface of the pad. The retracted position prevents the post from interfering with the bone contacting surface of the femoral component and the distal femur during impaction.

The present disclosure, in one form thereof, comprises, in combination, a family of distal femoral components comprising a first distal femoral component and a second distal femoral component, the first distal femoral component having a first distal femoral component bone contacting surface defining a first bone contacting surface configuration, and the second distal femoral component having a second distal femoral component bone contacting surface defining a second bone contacting surface configuration different from the first bone contacting surface configuration, each of the first and the second distal femoral components including a proximal surface configured to be positioned against a distal end of a femur and an opposite distal surface comprising a medial distal condyle and a lateral distal condyle, each of the first and the second distal femoral components including a wall defining a notch extending from the proximal surface to the distal surface and disposed between the medial distal condyle and the lateral distal condyle, the wall comprising an anterior end, a medial end, and a lateral end. The combination of this form of the present disclosure also includes an instrument for at least one of inserting, extracting, and impacting a selected one of the first distal femoral component and the second distal femoral component, the instrument having a proximal end and a distal end, the instrument including a handle extending between the proximal end of the instrument and the distal end of the instrument, a proximal surface having an opening therethrough, the proximal surface configured to contact the distal surface of the selected one of the first distal femoral component and the second distal femoral component when the selected one of the first distal femoral component and the second distal femoral component is seated with the instrument, a post slidably coupled to the handle, the post having a locking end extendable through the opening in the proximal surface, the locking end having a locking lip extending transversely from the post, the post movable between a locked position in which the lip is positioned a first distance from the proximal surface and an unlocked position in which the lip is positioned a second distance from the proximal surface, the second distance greater than the first distance, when the post is in the unlocked position, the post is rotatable with respect to the handle from a first position to a second position, wherein, with the post maintaining the first position, the instrument is capable of cooperating with the first bone contacting surface configuration of the first distal femoral component to lock the first distal femoral component to the instrument and wherein, with the post maintaining the second position, the instrument is capable of cooperating with the second bone contacting surface configuration of the second distal femoral component to lock the second distal femoral component to the instrument, and a locking actuator operatively engaged with the post, the locking actuator operable to move the post between the locked position and the unlocked position.

The present disclosure, in another form thereof, comprises, in combination, a femoral component having a proximal bone contacting surface for placement against a distal end of a femur and an opposite distal articulation surface including a medial condyle and a lateral condyle. The combination of this form of the present disclosure also includes an instrument for inserting and impacting the femoral component, the instrument having a proximal end and a distal end, the instrument comprising, a handle extending between the proximal end of the instrument and the distal end of the instrument, a proximal surface having an opening therethrough, the proximal surface sized and shaped to seat with the medial condyle and the lateral condyle of the femoral component, a post slidably coupled to the handle, the post having a locking end extendible through the opening in the proximal surface of the instrument, the locking end having a locking lip extending transversely from the post, the post moveable between a retracted position in which the lip is positioned at a first distance distally spaced from the proximal surface of the instrument and an exposed position in which the lip is positioned at a second distance proximally spaced from the proximal surface of the instrument, whereby with the lip in the retracted position, the proximal surface of the instrument is capable of use as an impaction surface for impacting the femoral component onto the distal end of the femur, and an actuator operably engaged with the post, the actuator operable to move the post between the retracted position and the exposed position.

The present disclosure, in a further form thereof, comprises a method of knee arthroplasty, the method including: selecting a distal femoral component, the distal femoral component comprising a proximal surface configured to be positioned against a distal end of a femur and an opposite distal surface including a pair of condyles, the distal femoral component including a wall defining a notch extending from the proximal surface to the distal surface and disposed between the pair of condyles; selecting an instrument including a locking lip and a proximal surface for contacting the distal femoral component; securing the distal femoral component to the instrument by positioning the locking lip against the proximal surface of the distal femoral component while the proximal surface of the instrument is positioned against the opposite distal surface of the distal femoral component; with the instrument, maneuvering the distal femoral component into a partially seated position with respect to the femur such that a space exists between the locking lip and the distal end of the femur; unlocking the instrument from the distal femoral component by moving the locking lip away from the proximal surface of the distal femoral component to release the locking lip from engagement with the proximal surface of the distal femoral component; retracting the locking lip into the instrument to a position distal of the proximal surface of the instrument whereby the instrument is usable as an impactor to seat the distal femoral component to the femur; and impacting the instrument to impact and seat the proximal surface of the distal femoral component to the femur.

BRIEF DESCRIPTION OF THE DRAWINGS

The above-mentioned and other features and advantages of this disclosure, and the manner of attaining them, will become more apparent and the disclosure itself will be better understood by reference to the following description of an embodiment of the disclosure taken in conjunction with the accompanying drawings, wherein:

FIG. 2 is a perspective view of a post of the inserter assembly of FIG. 1, including a locking lip at a proximal end and an annular notch at a distal end;

FIG. 3 is a fragmentary, radial elevational view of the distal end of the post of FIG. 2 showing the rotation of pins about the annular notch and the respective seating of pins in indents formed in a distal wall defining the annular notch;

FIG. 4 is a cross-sectional view taken line 4-4 of FIG. 3 showing the positioning of pins within the indents of the distal wall defining the annular notch;

FIG. 15A is a fragmentary, cross-sectional view of a handle assembly of the femoral component instrument of FIG. 11 in a fully open position;

FIG. 15B is a fragmentary, cross-sectional view of a handle assembly of the femoral component instrument of FIG. 11 in a locked, closed position;

Figure 1:
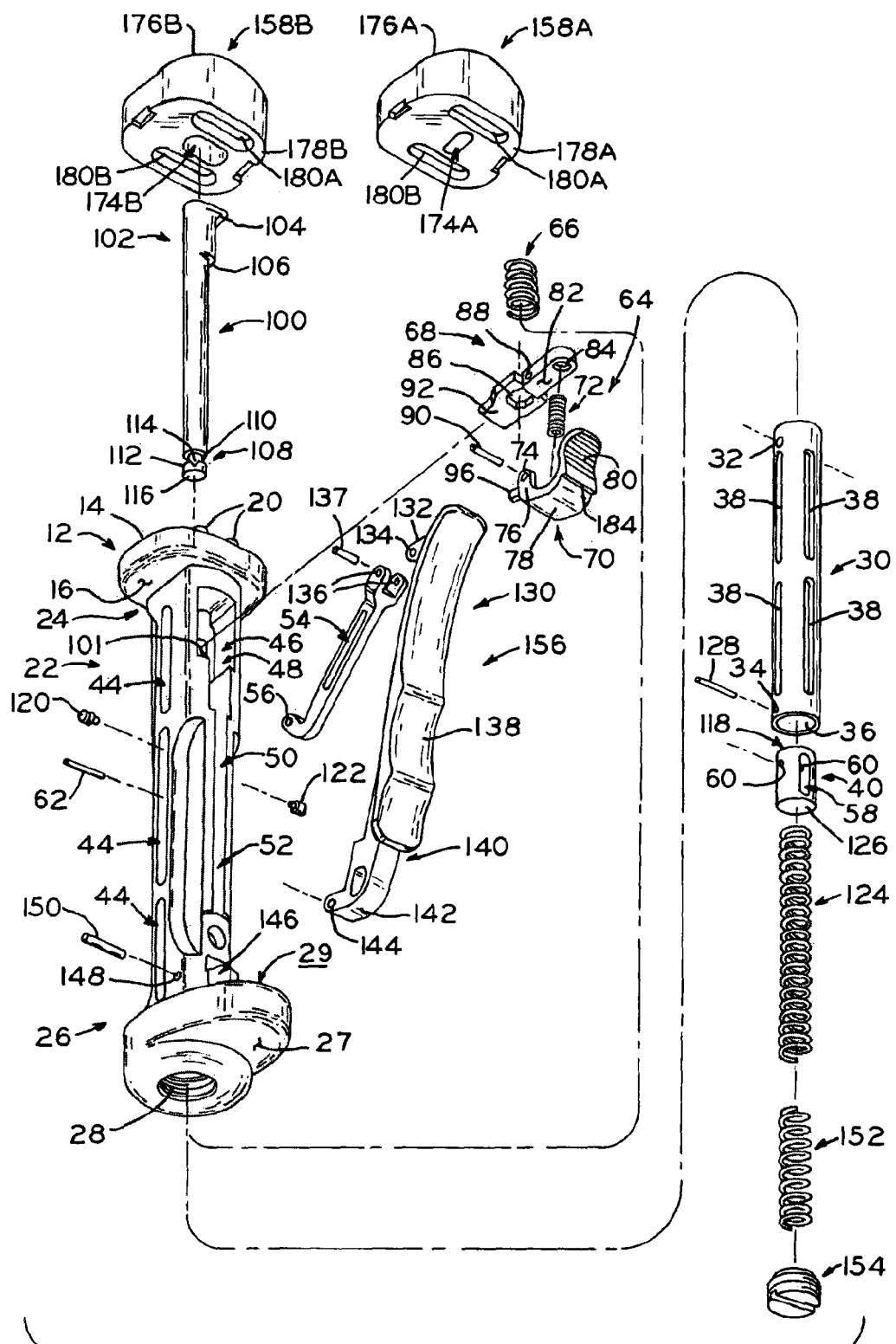
FIG. 1 is an exploded perspective view of an inserter assembly according to the present disclosure.

Corresponding reference characters indicate corresponding parts throughout the several views. The exemplification set out herein illustrates exemplary embodiments of the invention in various configurations, and such exemplifications are not to be construed as limiting the scope of the invention in any manner.

DETAILED DESCRIPTION

The present disclosure uses anatomic points of reference to describe the instrument herein. For example, the terms proximal and distal are used with reference to a distal femoral bone that the instrument is to be positioned against (the proximal end of the instrument being the end that, when the instrument is in use, is closest to the distal femoral bone while the distal end of the instrument is the end that is farthest from the distal femoral bone).

Disclosed is an inserter for interchangeable use with PS and CR femoral components. The inserter includes a rotatable post having a locking lip extending transversely from the post at a locking end for interchangeable engagement with either PS or CR femoral components. In an unlocked position, the lip, via rotation of the post, may rotate to a selected position.

The locking end of the post keys to a pad aperture such that rotation of the pad dictates a corresponding rotation of the post to one of two securement positions appropriate to the prosthesis type corresponding to the chosen pad. In an exemplary embodiment, a CR pad includes a slot through which the locking end of the post can extend in a first orientation relative to the instrument when the CR pad is secured to the instrument. In this embodiment, a PS pad will include a slot through which the locking end of the post can extend which, when the PS pad is secured to the instrument, will be oriented transverse to the aforementioned first orientation.

The inserter of the present disclosure may act as an impactor. The post of the inserter from which the locking lip extends is capable of movement from an external, exposed position proximal to the proximal pad surface to an internal, retracted position distal to the proximal pad surface. The retracted position prevents the post from interfering with the femoral component and the distal femur during impaction.

Referring to FIG. 1, distal end 26 of inserter assembly 10 includes opposing impaction surfaces 27, 29. Impaction surface 29 is oriented so that it may be struck to effect extraction of a femoral component from a femur. Similarly, impaction surface 27 is oriented so that it may be struck to seat a femoral component in a final seated position against a femur.

Figure 8:
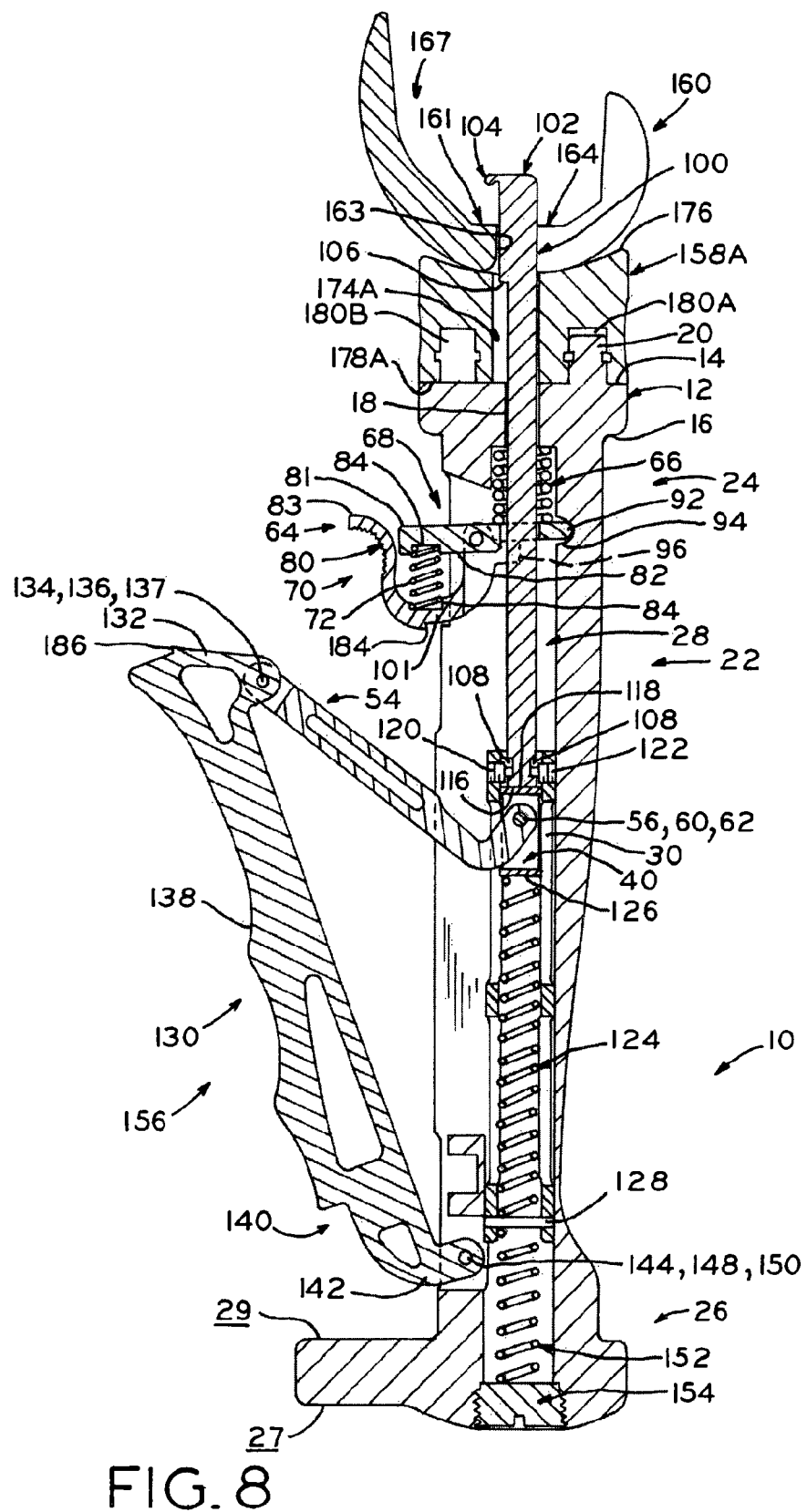
FIG. 8 is a cross-sectional view taken along line 8-8 of FIG. 6A.
Figure 9:
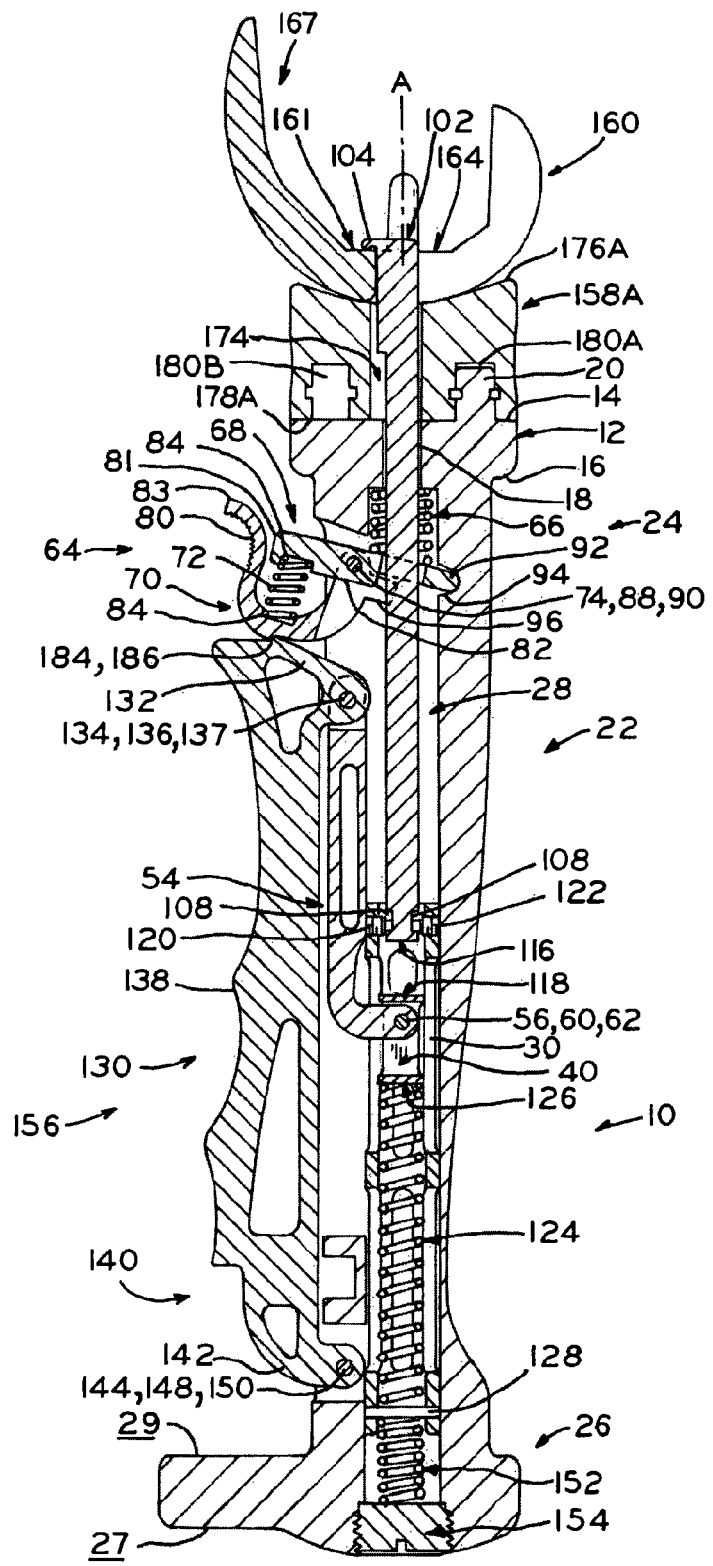
FIG. 9 is a cross-sectional view illustrating the inserter assembly locked to a CR femoral component.

Referring to FIGS. 1, 8, and 9, inserter assembly 10 includes base assembly 12 having a proximal surface 14 and a distal surface 16, between which aperture 18 (FIGS. 8, 9) extends. Aperture 28 (FIG. 1) extends from proximal end 24 of handle 22 to distal end 26 of handle 22 and is aligned with and intersects aperture 18 (FIGS. 8, 9) of base assembly 12. Pegs 20 (FIG. 1) extend proximally from proximal surface 14 of base assembly 12. In alternative embodiments, pegs 20 could be disposed on distal surfaces 178A, 178B of pads 158A, 158B, and corresponding apertures could be disposed in proximal surface 14 of base assembly 12. Handle 22 extends from proximal end 24 to distal end 26.

Referring to FIGS. 1 and 4, barrel 30 includes opposing pin apertures 32 at a proximal end and opposing pin apertures 34 at a distal end, each respectively positioned for receipt of pins as described further below. The pins of this disclosure effect rotatable linkages such as described below by having an outer diameter that is smaller than an inner diameter of the apertures through which a pin is inserted. Longitudinal aperture 36 extends from the proximal end to the distal end of barrel 30 and is defined by an interior annular wall. Slots 38 extend from an exterior surface of barrel 30 completely through the wall defining longitudinal aperture 36.

Referring to FIGS. 1 and 8, piston 40 is configured for receipt through aperture 36 of barrel 30 to define a first part of barrel and piston assembly 42. Barrel and piston assembly 42 is then received through aperture 28 at distal end 26 of handle 22 and inserted proximally through aperture 28 towards base assembly 12. Handle 22 includes a plurality of elongated grooves and slots 44 extending between proximal end 24 and distal end 26. A particular elongated groove 46 includes top portion 48, intermediate portion 50, and bottom portion 52.

Interior link lever 54 includes a piston linking end having pin aperture 56, the piston linking end receivable through groove 46 (FIG. 1) of handle 22, through slot 38 of barrel 30 and through elongated slot 58 of piston 40 for alignment of pin apertures 60 of piston 40 with pin aperture 56 of the piston linking end of interior link lever 54. A pair of opposing elongated slots 38 of barrel 30, spaced from a separate slot 38 that receives interior link lever 54, align with apertures 60 of piston 40 and aperture 56 of interior link lever 54. Pin 62 is then inserted through the pair of opposing elongated slots, apertures 60 of piston 40, and aperture 56 of interior link lever 54 to rotatably connect interior link lever 54 to piston 40.

Locking assembly 64 is assembled within a proximal end of handle 22. Spring 66 is first received through top portion 48 of groove 46 and into aperture 28 of handle 22 to rest against a counterbore formed between aperture 28 and aperture 18 (FIGS. 8, 9) of handle 22 at a proximal end of handle 22. Locking assembly 64 (FIG. 1) includes locking plate 68, lever 70 and spring 72. Lever 70 includes a set of pin apertures 74, each on a pair of opposing flanges 76, a bottom extension 78, and a proximally extending grip 80. Distal surface 82 of locking plate 68 and proximal surface 83 (FIGS. 8, 9) of bottom extension 78 include mutually-facing circular indents 84 (shown in FIGS. 1, 8, and 9) configured to receive spring 72 as illustrated, e.g., in FIG. 8.

Locking plate 68 is an elongate member including proximal surface 81 (FIGS. 8, 9) and distal surface 82. Referring to FIG. 1, distal surface 82 includes circular indent 84 configured to receive a proximal end of spring 72. Aperture 86 extends from proximal surface 81 to distal surface 82 of locking plate 68 and is separated from indent 84 via pin aperture 88. Aperture 88 is configured for alignment with pin apertures 74 of flanges 76 of lever 70, such that rotatable pin 90 may be received through pin apertures 74 and 88 to connect lever 70 to locking plate 68 with spring 72 disposed between lever 70 and locking plate 68. Locking plate 68 includes extension plate 92 configured for receipt within notch 94 defined by internal side walls within handle 22. Stop 96 of lever 70 acts as a stop against distal surface 82 of locking plate 68. Referring to FIGS. 8 and 9, post 100 may be disposed between and against a pair of stops 96 such that each stop 96 is offset relative to post 100.

A tool may be used to maneuver spring 66 out of the way when locking assembly 64 is inserted through top portion 48 of groove 46 of handle 22 such that extension plate 92 is inserted into notch 94 to prevent axial slide of locking assembly 64 within handle 22. Post 100 is then dropped through aperture 18 (FIGS. 8, 9) of base assembly 12, through aperture 28 of handle 22, through spring 66, and through aperture 86 of locking assembly 64. Referring to FIGS. 1 and 8, locking assembly 64, when inserted through top portion 48 of groove 46, may distally rest against ledge 101, which provides a stop against which spring 66 biases locking assembly 64.

As shown in FIG. 2, post 100 includes locking lip 104 extending transversely relative to the longitudinal axis of post 100 at proximal locking end 102. Locking lip 104 extends transversely to longitudinal axis A of post 100 and does not extend from the entire perimeter of post 100. Disposed below locking lip 104 is a first portion of post 100 having a cross section that has a greater area than a cross section disposed below the first portion such that shoulder 106 is defined therebetween. Shoulder 106 is capable of abutting a proximal surface 14 of base assembly 12. At a distal end, post 100 includes annular notch 108 defined between proximal wall 110 and distal wall 112, distal wall 112 including four V-shaped indents 114. In alternative embodiments, indents 114 can be U-shaped. Distal end 116 of post 100 is a solid surface that will initially abut solid proximal end 118 of piston 40 and annular notch 108 will be in alignment with pin apertures 32 (FIG. 1) of barrel 30 through which first and second notch pins 120 and 122 (FIGS. 3 and 4), respectively, may be received to pin barrel 30 to post 100, preventing substantial axial displacement, but allowing for rotational displacement, of post 100 with respect to barrel 30. The rotation of post 100 within barrel 30 about axis A will be described further below.

Referring to FIGS. 1, 8 and 9, a stiff distal spring 124 is inserted through a distal end of barrel 30 to abut distal end 126 of piston 40. Distal of a distal end of spring 124, pin 128 is received through pin aperture 34 of barrel 30 such that the distal end of spring 124 abuts and rests against pin 128. Distal spring 124 is stiffer than spring 152, described further below, i.e., spring 124 has a spring constant that is greater than the spring constant of spring 152, such that spring 152 is more easily compressed than spring 124. The reason for this difference in spring constant between spring 124 and spring 152 will be full described with respect to the operation of inserter assembly 10, which is described in detail below.

Exterior link lever 130 includes a proximal end having a flange 132 through which pin aperture 134 extends. Pin aperture 134 is disposable between and positionable for alignment with pin apertures 136 of interior link lever 54. Pin 137 is received by aligned pin apertures 134 and 136. Exterior link lever 130 further includes grip 138 and distal end 140. Distal end 140 includes flange 142 including pin aperture 144 extending therethrough. Distal end 140 is configured for receipt through distal groove 146 of handle 22 such that pin aperture 144 may be aligned with opposing pin apertures 148 (FIGS. 1 and 5) of a distal end of handle 22 and pin 150 may be received through aligned apertures 148 and 144 to pivotally connect exterior link lever 130 to handle 22. Referring to FIG. 8, apertures 148 of handle 22 are disposed exterior of aperture 28 of handle 22 so that apertures 148 will not interfere with movement of the pin and barrel assembly within aperture 28 of handle 22.

Spring 152 is inserted through aperture 28 at a distal end of handle 22, and threaded nut 154 is inserted to threadably engage threaded interior walls of distal end of aperture 28 of handle 22 such that a distal end of spring 152 may rest against a proximal surface of threaded nut 154.

Figure 5:
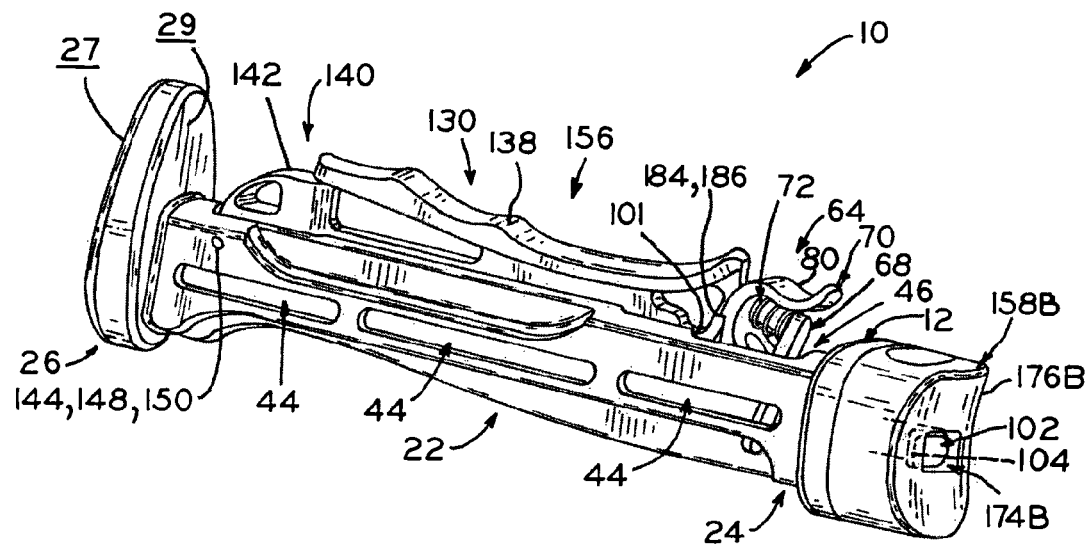
FIG. 5 is a perspective view of the inserter assembly of FIG. 1, with the post retracted internally of a proximal pad surface so that the inserter can be used as an impactor.
Figure 6A:
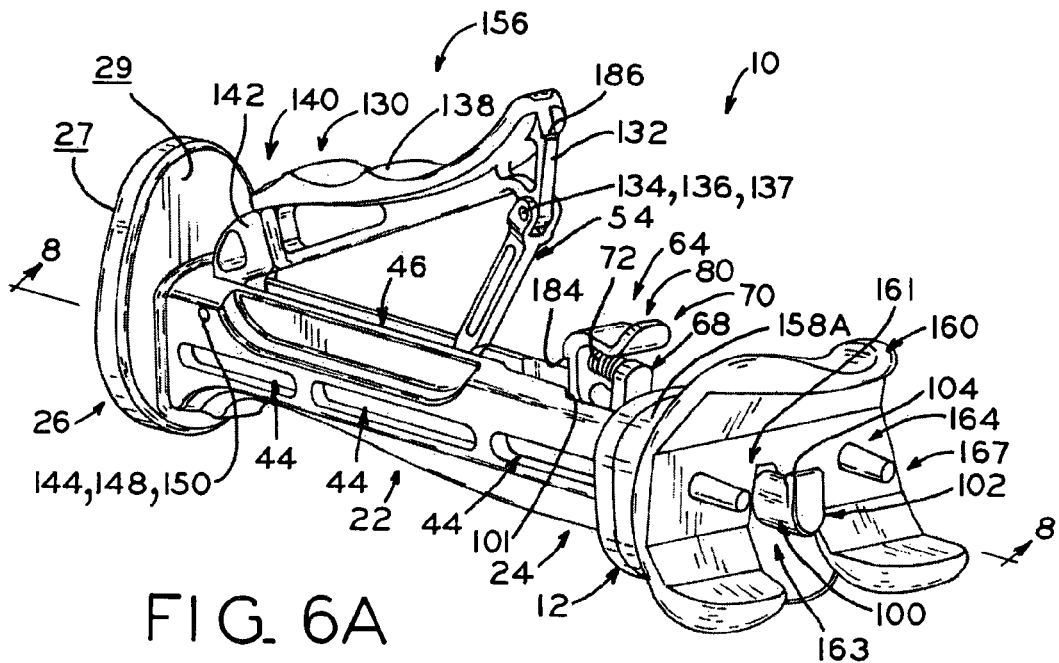
FIG. 6A is a perspective view of the inserter assembly of FIG. 1 configured for use with a CR femoral component.

Referring to FIGS. 5 and 6A, inserter assembly 10 is movable between an open position (FIG. 6A) and a closed position (FIG. 5). Locking actuator 156 comprised of exterior link lever 130 and interior link lever 54 (FIG. 6A) is engaged to post 100 (as described above) such that when locking actuator 156 is in the open position of FIG. 6A, post 100 is in an extended position, or an unlocked position, a certain distance away from the proximal surface of pad 158. If a femoral component is not present, as shown in FIG. 5, locking actuator 156 may be utilized to retract post 100 within inserter assembly 10 so that post 100 does not extend beyond proximal surface 176B of instrument 10. Pressing locking actuator 156 towards handle 22 to close locking actuator 156 causes interior link lever 54 to rest in groove 46 of handle 22, and exterior link lever 130 to rest above interior link lever 54. Locking actuator 156 is locked to locking assembly 64 via an intermeshing of two respective shoulders: shoulder 184 of locking assembly 64 and shoulder 186 of locking actuator 156 (FIG. 9), as further described below.

Figure 6B:
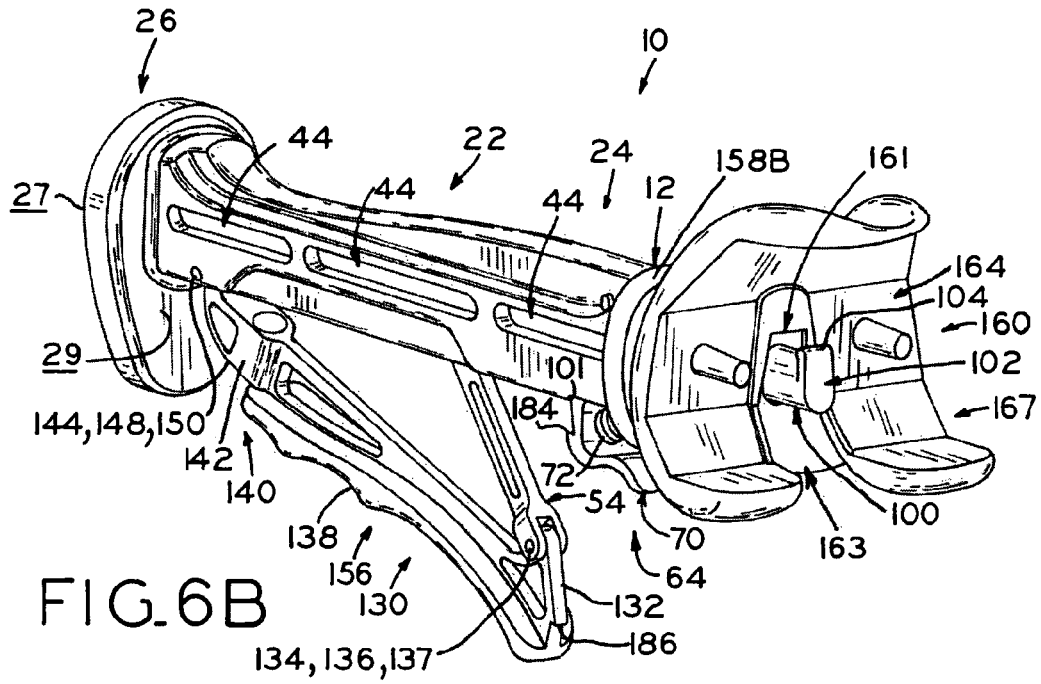
FIG. 6B is a perspective view of the inserter assembly of FIG. 6A, showing the post in an alternative position for use with a CR implant.

Referring to FIGS. 6A, 6B and 8, to move locking actuator from an open position to a closed position, as shown in FIG. 9, force is applied against grip 138 of exterior link lever 130. The applied force causes exterior link lever 130 to rotate about pin 150 while being pushed inwardly towards groove 46 of handle 22. The inwards movement results in another rotation about pin 137, allowing force to be translated from exterior link lever 130 to interior link lever 54 so that interior link lever 54 moves inwardly towards groove 46. As interior link lever 54 is linked to piston 40 via rotatable pin 62, a downwards force is applied to piston 40, as described below.

Referring to FIGS. 8 and 9, when interior link lever 54 is pressed into groove 46, pin and barrel assembly 42 (FIG. 1) moves distally along with post 100. Specifically, when interior link lever 54 is pressed into groove 46, the end of interior link lever 54 having pin aperture 56 is moved distally toward impaction surface 27 of inserter assembly 10. The force applied by interior link lever 54 to piston 40 opposes the biasing force of springs 124, 152. Because spring 124 is stiffer than spring 152, spring 152 is compressed to allow piston 40 to travel distally through aperture 28 of handle 22. Compression of spring 152 allows pin 128 to move distally from the position illustrated in FIG. 8 to the position illustrated in FIG. 9. This movement of pin 128 consequently causes distal movement of barrel 30 (to which pin 128 is secured) and post 100, which is pinned to barrel 30 as described above.

As illustrated in FIG. 9, travel of pin 128 is limited when femoral component 160 is associated with inserter assembly 10 for securement thereto. Specifically, with femoral component 160 positioned as illustrated in FIG. 9, locking lip 104 cooperates with a bone contacting surface of femoral component 160 to secure femoral component 160 to inserter assembly 10. As locking lip 104 engages distal facet 164 of proximal bone contacting surface 167 of femoral component 160, further distal travel of pin 128 is precluded owning to the pinned connection of barrel 30 to post 100. When this occurs, further distal travel of piston 40 acts against spring 124 to compress spring 124 which, in turn, supplies a locking force to femoral component 160.

If femoral component 160 is not present, travel of pin 128 will not be limited as illustrated in FIG. 9. If femoral component 160 is absent and locking actuator 156 is actuated from an open position (see, e.g., FIGS. 6A, 6B, 7A, and 7B) to the closed position illustrated in FIG. 5, travel of pin 128 will continue distally from the position illustrated in FIG. 9, for example, thereby further moving post 100 distally until locking lip 104 is retracted into inserter assembly 10 such that locking lip 104 does not extend beyond proximal surface 176B, as illustrated in FIG. 5. Retraction of locking lip 104, as illustrated in FIG. 5, allows inserter assembly 10 to be utilized as an impaction instrument to fully seat a femoral component. Importantly, with locking lip 104 recessed from the proximal end of inserter assembly 10, locking lip 104 will not be adjacent the prepared distal end of the femur and will not be available to interfere with the femoral component and the distal femur during impaction.

Referring to FIG. 9, when locking actuator 156 is in a closed or locked position, a V-shaped shoulder 186 abuts a corresponding V-shaped shoulder 184 of locking assembly 64 to lock locking actuator 156 in place against locking assembly 64. To overcome this intermeshed locking, grip 80 of lever 70 may be compressed upwardly applying a force against spring 72 and spring 66 until shoulder 186 of locking actuator 156 begins to space away from shoulder 184 of lever 70 and clears shoulder 184 of lever 70 such that locking actuator 156 is able to be distanced away from locking assembly 64. Releasing grip 80 allows spring 72 and spring 66 to be restored to their normally biased positions illustrated, e.g., in FIG. 8.

While post 100 is connected to barrel 30, such that a significant longitudinal displacement from barrel 30 is prevented, post 100 is capable of a rotational displacement about and within barrel 30. Referring to FIG. 2, and as described above, post 100 includes a distal end having annular notch 108 defined by proximal end wall 110 and distal end wall 112, distal end wall 112 including four spaced apart indents 114 that may be, for example, V-shaped indents. In alternative embodiments, indents 114 can be U-shaped. The four spaced apart indents include two pairs of opposing indents, each indent spaced 90° from one another.

Distal wall 112 includes peaks and indents 114 spaced in an alternating manner along distal wall 112. The peaks and indents 114 are each spaced along distal wall 112 and are each part of distal wall 112. Extending radially inwardly from barrel 30 are two 180° opposed pins 120, 122 as illustrated, e.g., in FIGS. 3 and 4. Referring to FIG. 8, spring 124 acts to bias piston 40 into engagement with post 100 in the open position of inserter assembly 10. In this position, piston 40 is urged by spring 124 against post 100, which causes pins 120, 122 (FIGS. 3 and 4) to be urged into contact with distal end wall 112. To effect rotation of locking lip 104 between the positions illustrated, e.g., in FIGS. 6A and 7A, post 100 is rotated, causing opposing pins 120, 122 to be axially displaced against the biasing force of spring 124 as they ride up one of the opposing ramps forming indents 114. Movement of pin 120 from one indent to another is illustrated in FIG. 3 which shows a first position of pin 120 in section followed by sequential illustrations of pin 120 as it rides up the ramp surface of indent 114 into engagement with distal end wall 112 and is finally seated in indent 114B. The above described rotation is also seen in FIG. 4, showing pins 120 and 122 in a seated position, and a possible rotation about arrows B in a first direction, or arrows C in an opposing second direction, such that the pins may slide up the ramps of the V-shaped indents in a first direction or in an opposing opposite second direction and slide across planar edges of the distal end wall when post 100 is being rotated to then be seated in the next pair of opposing indents.

As described above, the inserter assembly of the present disclosure is interchangeable between CR and PS femoral components, utilizing a respective CR or PS modular pad with each respective component. Further, the femoral component may be of a variety of sizes and still may be seated against the same respective CR or PS modular pad. Referring to FIGS. 6A, 6B, 8, and 9, CR femoral component 160 is shown for seating against CR receiving modular pad 158A where post 100 is shown in an unlocked position prior to such seating. Whether it is a CR femoral component 160 of FIGS. 6A, 6B, 8, and 9 or PS femoral component 162 of FIGS. 7A, 7B, and 10, the femoral component will contact a respective pad 158A or 158B. In an exemplary configuration, the contact may occur at anterior and posterior contact points on each condyle of the femoral component, which contact points are, for example, equidistantly spaced from the axis along which post 100 applies a downwards force via locking lip 104. In one configuration, the contact may occur at the distal most points of each of the medial and lateral femoral condyles. In this configuration, the axis along which post 100 applies a downward force via locking lip 104 to the femoral components intersects a line formed by the distal most points of the femoral component that contact the pad. In other configurations, the axis along which post 100 applies a downward force via locking lip 104 to the femoral components may be offset up to approximately 3 mm from a line formed by the distal most points of the femoral component that contact the pad. In both configurations, the securement force supplied by post 100 does not impart a torque to the femoral component secured to insertion instrument 10.

Figure 7A:
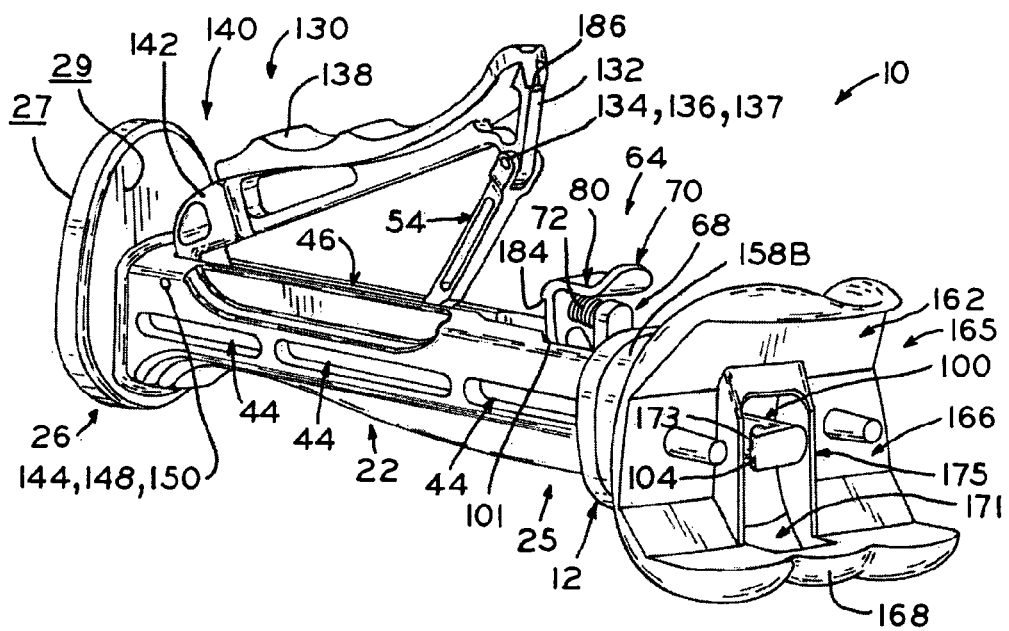
FIG. 7A is a perspective view of the inserter assembly of FIG. 1 configured for use with a PS femoral component.
Figure 7B:
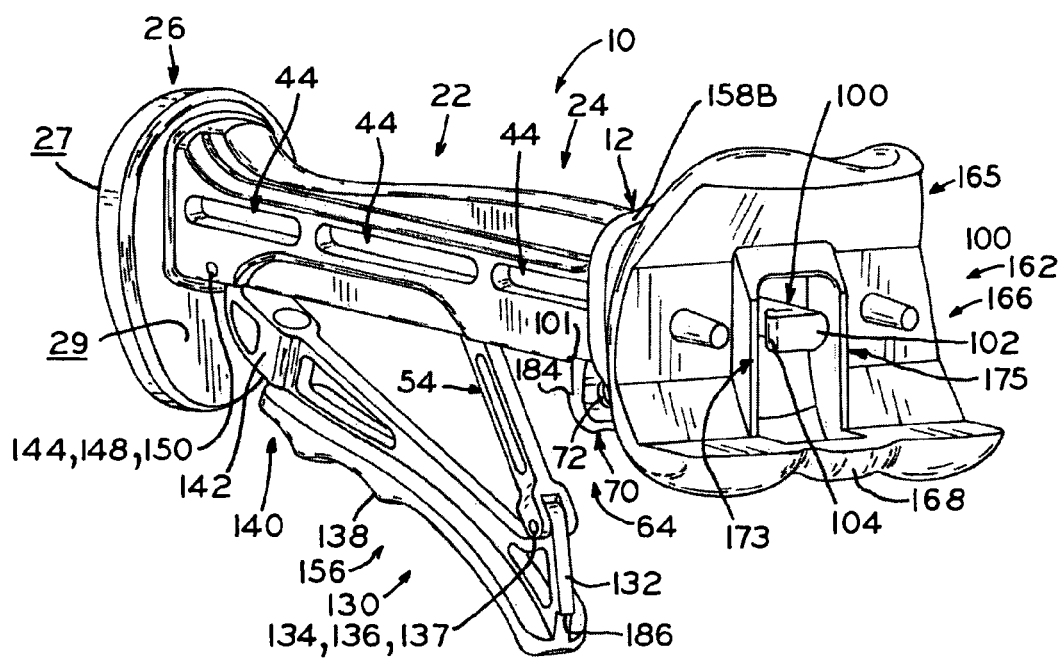
FIG. 7B is a different perspective view of the embodiment of FIG. 7A, showing the post in an alternative position for use with a PS implant.

Further, as illustrated in FIGS. 7A and 7B, lip 104 may have a planar distal surface for seating against a planar flat surface of the intercondylar notch. In an instance, the femoral component may initially be slightly askew on the pad such that the planar distal surface of lip 104 includes portions angled with respect to the planar flat surface of the intercondylar notch. An application of force via lip 104 against the planar flat surface of the intercondylar notch may cause the skewed lip to be adjusted until the two planar surfaces are flush against one another and not askew.

As locking lip 104 of post 100 is able to rotate, locking lip 104 accommodates the differences between the respective distal most points of the CR and PS femoral components. Referring back to FIGS. 6A and 6B, which show CR modular pad 158A receiving CR femoral component 160, post 100 is rotated such that a locking lip 104 is positioned above a portion of anterior end 161 of a wall defining intercondylar notch 163 of femoral component 160. As shown in FIGS. 8 and 9, and as described above, post 100 may be actuated via moving locking actuator 156 from an open, unlocked position (FIG. 8) to a closed, locked position (FIG. 9), allowing femoral component 160 to be seated against pad 158A. Locking lip 104 of post 100 applies a load for different sizes of femoral component 160 at a portion of anterior end 161 of the wall defining notch 163, which is approximately aligned with the line formed by the distal most points of femoral component 160.

Figure 10:
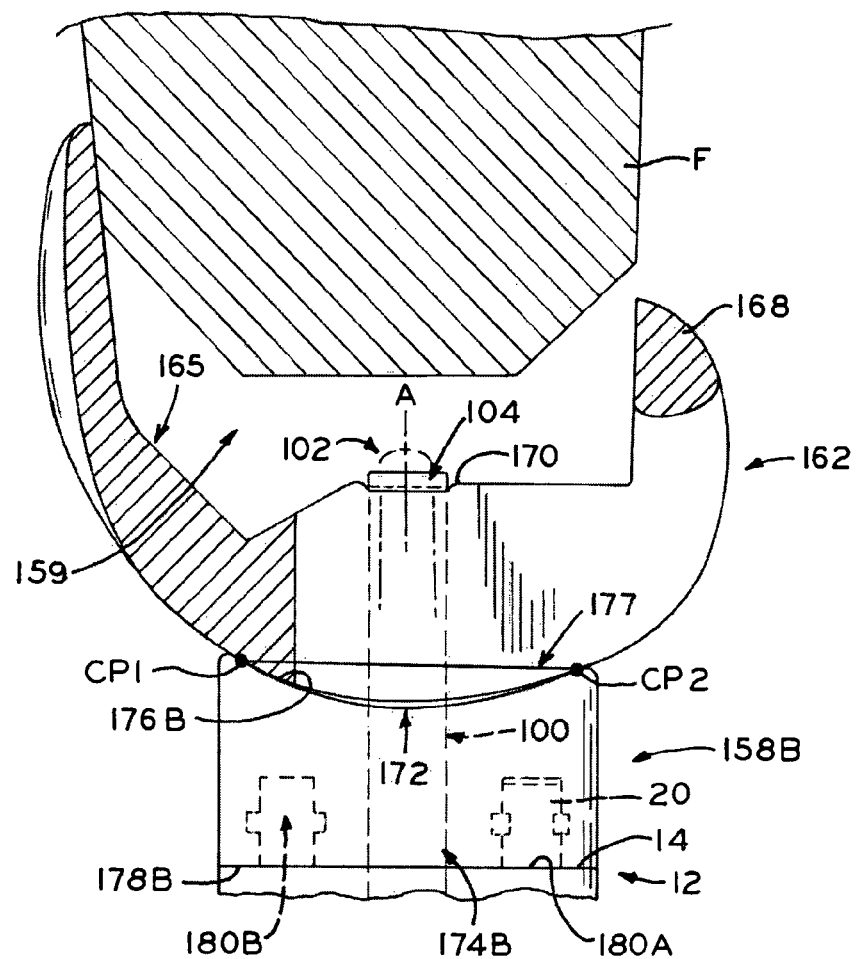
FIG. 10 is a partial sectional view illustrating insertion of a PS femoral component onto a femur.

FIGS. 7A and 7B show PS specific femoral component 162 including a cam 168 at a Posterior Cruciate Ligament ("PCL") region, and distal facet 166 of proximal post contacting surface 165. In FIG. 10, femoral component 162 is seated against PS specific pad 158B in a locked position, as shown by the placement of locking lip 104 against either a medial or a lateral notch 170 within the walls defining the intercondylar notch of PS specific femoral component 162. Referring to FIGS. 7A and 7B, an alternative placement may occur against a portion of medial or lateral ends or flat surfaces of the wall defining intercondylar notch 171 such as at medial end 173 or at lateral end 175. In a configuration, the load applied via locking lip 104 is a downwards load applied along a portion of medial end 173 or lateral end 175 of the wall defining intercondylar notch 171, such as along notch 170 of FIG. 10. The portion to which the load is applied is parallel to and aligned with the line including the distal most points of the distal condyles of PS specific femoral component 162. In other embodiments, the portion to which the load is applied can be offset up to approximately 3 mm from the line including the distal most points of the distal condyles of PS specific femoral component 162, as described above.

Comparing FIGS. 9 and 10, the line including the distal most points of the respective CR and PS femoral components can be either offset from axis A of post 100 (FIG. 9) or aligned with axis A of post 100 (FIG. 10). For the CR component as shown in FIG. 9, the distal most points of the distal condyles of femoral component lie along a line parallel to a distal facet of the femoral component. An axis normal to the distal facet of the femoral component and intersecting one of the distal most points of the distal condyles will be substantially parallel to the direction of force applied by locking lip 104. The force applied by locking lip 104 is exerted on the femoral component such that no moment is imparted on the femoral component.

Another exemplary configuration is shown in FIG. 10 in which the distal most points of the femoral component do not contact a pad. When a femoral component is seated against the respective femoral component modular pad, there are two points of contact per condyle such that four contact points in total exist from anterior to posterior for each condyle. The contact points define a periphery defining space 172 between the femoral component and the pad. When PS specific femoral component 162 is seated against PS receiving modular pad 158B, PS specific component 162 will seat against anterior and posterior contact points of modular pad 158B on each of the distal condyles of component 162. The contact points of a pair of contact points on a respective condyle such as contact points CP1 and CP2 shown in FIG. 10 are equidistant from axis A against which load is downwardly applied via locking lip 104 to intersect contact line 177 formed by contact points CP1 and CP2. Thus, when a load is applied via post 100 as described above, the femoral component will not rock within the seating. In an alternative embodiment, the contact points of a pair of contact points on a respective condyle such as contact points CP1 and CP2 shown in FIG. 10 are offset up to approximately 3 mm from axis A against which load is downwardly applied via locking lip 104 to intersect contact line 177 formed by contact points CP1 and CP2.

In certain embodiments, the femoral component contacts the anterior and posterior edges of the modular pad for a variety of sizes of the femoral component. At a smallest size, the femoral component has a distal condyle radius that is equal to the radius of the modular pad. With such a size, the femoral component may contact the pad at the distal most points of the distal condyles of the component. In such a situation, application of force downwards against a line including the distal most points assists to prevent rocking of the femoral component. As the size of the femoral component increases, the radius of the femoral component increases with respect to the associated radius of the modular pad, and anterior and posterior contact points, all illustrated, e.g., in FIG. 10 and described above are formed.

Referring to FIG. 10, inserter assembly 10 may partially seat femoral component 162 against prepared distal femoral bone F such that gap 159 exists between post 100 and a distal cut of bone F while anterior and posterior portions or cuts of distal bone F contact respective anterior and posterior facets of proximal bone-contacting surface 165 of femoral component 162. After partial seating of femoral component 162 to bone F, locking actuator 156 (FIGS. 7A and 7B) may be unlocked as described above to move post 100 proximally into gap 159 to remove post 100 from engagement with notch 170 of femoral component 162. Locking actuator 156 may then be closed to retract post 100 within inserter assembly 10 and distally from proximal surface 176B of pad 158B as described above so that proximal surface 176B presents a smooth, uninterrupted surface ready to impact femoral component 162 into a final seating via an impaction against impaction surface 27 (FIGS. 7A and 7B). Further, referring to FIGS. 5 and 10, by retracting post 100 distally from proximal surface 176B of pad 158B, post 100 will not interfere with gap 159 between the distal end of bone F and proximal bone-contacting surface 165 (FIGS. 7A and 7B). Thus, gap 159 may be closed upon impaction so that bone F is flush with and contacts proximal bone-contacting surface 165 in a final seating.

When a femoral component is not provided for seating engagement to the pad, the pad may assist with rotation of post 100 to align post 100 to an appropriate securement position dependant on whether the pad is CR pad 158A or PS pad 158B, as described below. Referring to FIGS. 1, 9 and 10, a proximal end of post 100 is keyed to pad aperture 174A, 174B running from proximal surface 176A, 176B to distal surface 178A, 178B of a respective modular pad 158A, 158B. Specifically, pad apertures 174A, 174B are elongate slots sized to accommodate locking lip 104 in the direction of elongation of the locking slots 174A, 174B. Opposing walls of pad apertures 174A, 174B which run parallel to the direction of elongation of pad apertures 174A, 174B are separated by a distance only slightly larger than width W of locking lip 104 (FIG. 2).

Therefore, when modular pad 158A or 158B is in a first position to receive proximal end 102 of post 100 such that proximal end 102 does not extend beyond the respective proximal surface 176A, 176B of pad 158A, 158B, pad 158A or 158B will be able to rotate about and above proximal surface 14 of base assembly 12, causing a corresponding rotation of post 100. When both the pad and post 100 are in a desired and appropriate securement position for the type of pad used, such as, for example, a position shown in FIG. 6A for CR pad 158A or a position shown in FIG. 6B for PS pad 158B, modular pad 158A or 158B is then pressed down upon proximal surface 14 of base assembly 12 such that one of two opposing peg receiving grooves 180A, 180B of either pad 158A or 158B (the peg receiving grooves for either pad utilizing the same reference numerals herein) receive pegs 20 on proximal surface 14 of base assembly 12 to lock modular pad 158A, 158B to base assembly 12 and prevent rotation of modular pad 158A, 158B on top of base assembly 12 of inserter assembly 10 while keying locking lip 104 of post 100 to a desired position.

The CR pad may include aperture 174 sized to receive proximal end 102 of post 100 including locking lip 104, and the CR pad aperture is rotated 90° relative to aperture 174B in the PS pad such that lip 104 is rotated to a desired seating for the chosen CR or PS pad. The CR pad aperture may extend between a pair of grooves 180A, 180B in a direction towards each groove 180A or 180B (and normal to a direction of the grooves), wherein each groove 180A, 180B is capable of receiving placement pegs 20 disposed on base assembly 12. In a configuration, for a CR pad receiving a CR femoral component, an appropriate securement position includes aligning locking lip 104 with an anterior portion of an intercondylar notch of the component, which is possible via positioning the CR pad on the inserter in one of two positions, each position defined by reception of placement pegs 20 within a different one of the pair of grooves 180A, 180B.

In another configuration, PS pad aperture 174B rotated 90° relative to CR pad aperture 174A is spaced between the pair of grooves 180A, 180B such that aperture 174B extends in the same direction as the grooves 180A and 180B (i.e., parallel to a direction of the grooves). Appropriate securement positions for a PS pad receiving a PS femoral component include aligning locking lip 104 with either a medial or a lateral portion of the intercondylar notch of the component. Such positions are possible via positioning a PS pad in one two positions, each position defined by reception of the placement pegs 20 within a different one of the pair of grooves 180A, 180B.

Advantageously, via rotation of post 100 and rotational adjustment of pad 158A or 158B such that either grooves 180A or grooves 180B receive pegs 20 of base assembly 12, the different positions shown in FIGS. 6A-7B allow for a user to select a position that permits easier use for the specific user. For example, the different positions of locking actuator 156 with respect to the orientation locking lip 104 may allow for both right and left-handed surgeons to select a personalized position most comfortable for surgery.

The keying pad aperture 174 is utilized with inserter assembly 10 such that locking lip 104 must be positioned in an appropriate securement position to allow attachment of the respective CR or PS pad to the inserter. Each modular pad 158A, 158B has a sufficient proximal height such that locking lip 104 cannot traverse pad aperture 174A, 174B and extend proximally from proximal surface 176A, 176B unless post pegs 20 are received in one of grooves 180A, 180B. With this in mind, modular pads 158A, 158B cannot be secured to insertion instrument 10 unless locking lip 104 is first rotated into a position corresponding to an appropriate position to lock a femoral prosthesis of the type associated with the particular modular pad. To preclude rotation of locking lip 104 out of this position once modular pad 158A, 158B is finally seated onto insertion instrument 10 as illustrated, e.g., in FIGS. 8 and 9, an end of post 100 between shoulder 106 and locking lip 104 (FIG. 2) is elongated such that the sidewalls of each pad aperture 174A, 174B which run parallel to the direction of elongation of pad apertures 174A, 174B cooperate with the above-defined end to preclude rotation of locking lip 104.

FIGS. 11-16C illustrate another exemplary embodiment. This embodiment of the present disclosure, similar to the embodiment illustrated in FIGS. 1-10, is a femoral component instrument for interchangeable use with PS and CR femoral components, which can be used as an inserter, impactor and extractor for use in the placement, impaction and extraction of a femoral prosthesis or femoral provisional component, for example. Referring to FIGS. 11-14, femoral component instrument 200 includes instrument body 202, handle assembly 204, rotatable post 206, and pad 208.

Figure 13:
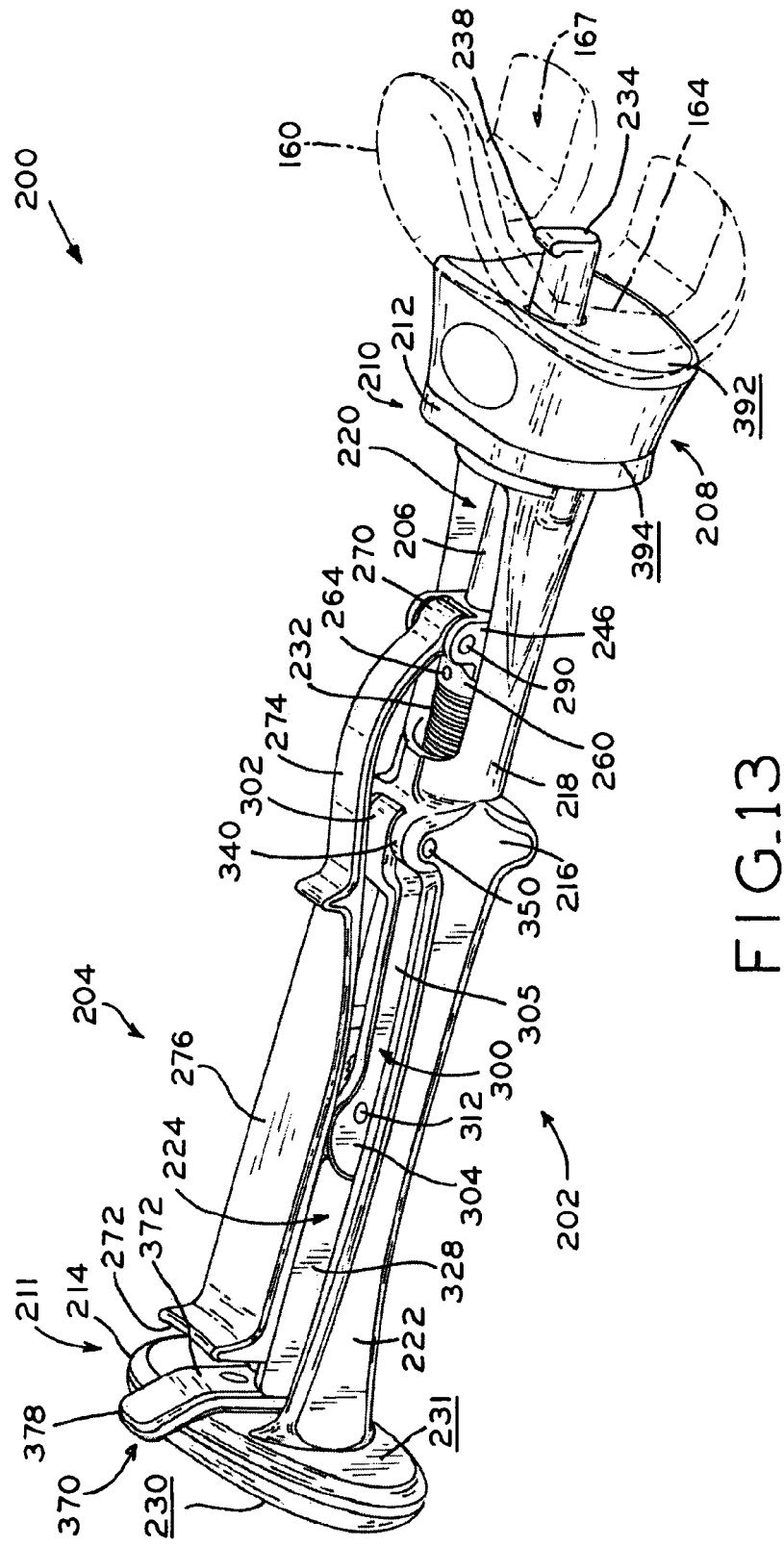
FIG. 13 is an assembled perspective view of the femoral component instrument of FIG. 11 in a locked, closed position, with a femoral component (shown in hidden lines) secured to the femoral component instrument.

In the following discussion, "proximal" refers to a direction generally toward the heart of a patient, and "distal" refers to the opposite direction of proximal, i.e., away from the heart of a patient. For purposes of this disclosure, the above-mentioned anatomical references are used in the description of the components of femoral component instrument 200 with reference to a desired operable use of the components in the body and with femoral component instrument 200 in a closed position as shown in FIGS. 13 and 14.

Referring to FIGS. 11-14, instrument body 202 includes instrument body proximal end 210, opposing instrument body distal end 211, pad plate 212 located at proximal end 210, impaction plate 214 located at distal end 211, and center body portion 216 located between proximal end 210 and distal end 211. Instrument body 202 includes proximal body wall 218 which defines proximal body cavity 220 and extends between pad plate 212 and center body portion 216. Instrument body 202 also includes distal body wall 222 which defines distal body cavity 224 and extends between center body portion 216 and impaction plate 214. Pad plate 212 defines pad plate aperture 226 which spans the extent of pad plate 212 such that pad plate aperture 226 is in communication with proximal body cavity 220. Center body portion 216 defines center body aperture 228 (FIG. 14) which spans the extent of center body portion 216 such that center body aperture 228 (FIG. 14) is between and in communication with each of proximal body cavity 220 and distal body cavity 224. Impaction plate 214 defines opposing impaction surfaces 230, 231. Impaction surface 231 is oriented so that it may be struck to effect extraction of a femoral component from a femur. Similarly, impaction surface 230 is oriented so that it may be struck to seat a femoral component in a final seated position against a femur.

As previously discussed with the embodiment illustrated in FIGS. 1-10, femoral component instrument 200 of the present disclosure is interchangeably useable with both CR and PS femoral components, utilizing a respective CR or PS modular pad, as appropriate. Further, the femoral component may be of a variety of sizes having a variety of thicknesses and still may be seated against the same respective CR or PS modular pad. Referring to FIGS. 11-14, pad 208 of femoral component instrument 200 is a CR modular pad for seating a CR femoral component such as CR femoral component 160 (shown in FIGS. 12 and 13 in hidden lines) thereto. In another embodiment, pad 208 of femoral component instrument 200 may be a PS modular pad for seating a PS femoral component thereto. In such an embodiment, a PS modular pad will have a pad aperture rotated 90° relative to CR pad aperture 390.

Figure 14:
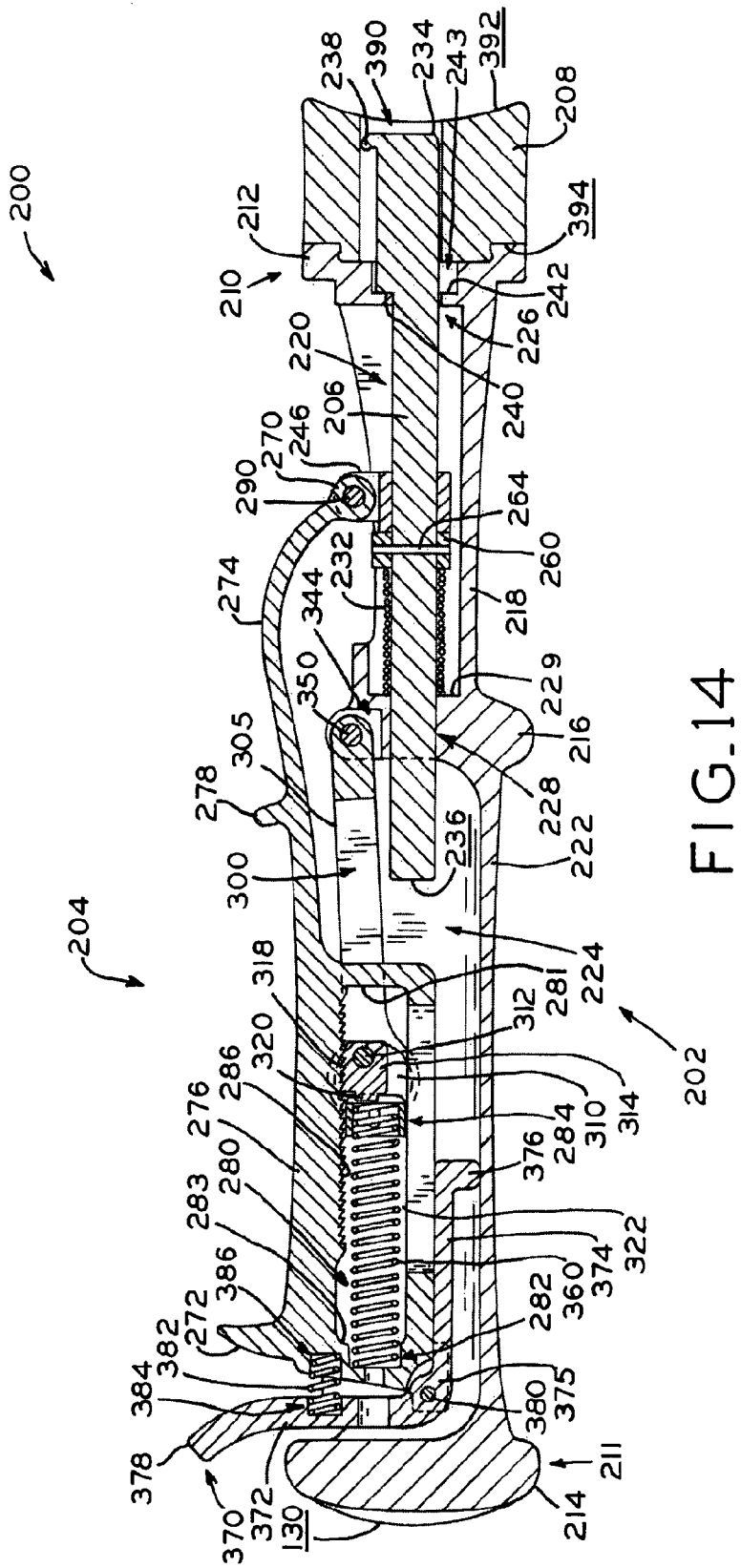
FIG. 14 is a cross-sectional view of the femoral component instrument of FIG. 11 in a locked, closed position, with a locking lip of a post of the femoral component instrument retracted within a pad of the femoral component instrument.

Referring to FIGS. 11-14, proximal body cavity 220 receives proximal body spring 232 therein such that a distal end of proximal body spring 232 abuts proximal wall 229 (FIG. 14) of center body portion 216. Post 206 includes post proximal end wall 234, opposing post distal end wall 236, and locking lip 238 extending transversely relative to the longitudinal axis of post 206 at post proximal end wall 234. Locking lip 238 does not extend about the entire perimeter of post 206. Disposed below locking lip 238 is a first portion of post 206 having a cross-section that has a greater area than a cross-section disposed below the first portion such that shoulder 240 is defined therebetween. Shoulder 240 is capable of abutting proximal surface 242 disposed in counterbore 243 of pad plate 212, as illustrated in FIG. 14. Post 206 also includes pin aperture 244 therein at a central portion of post 206.

Figure 11:
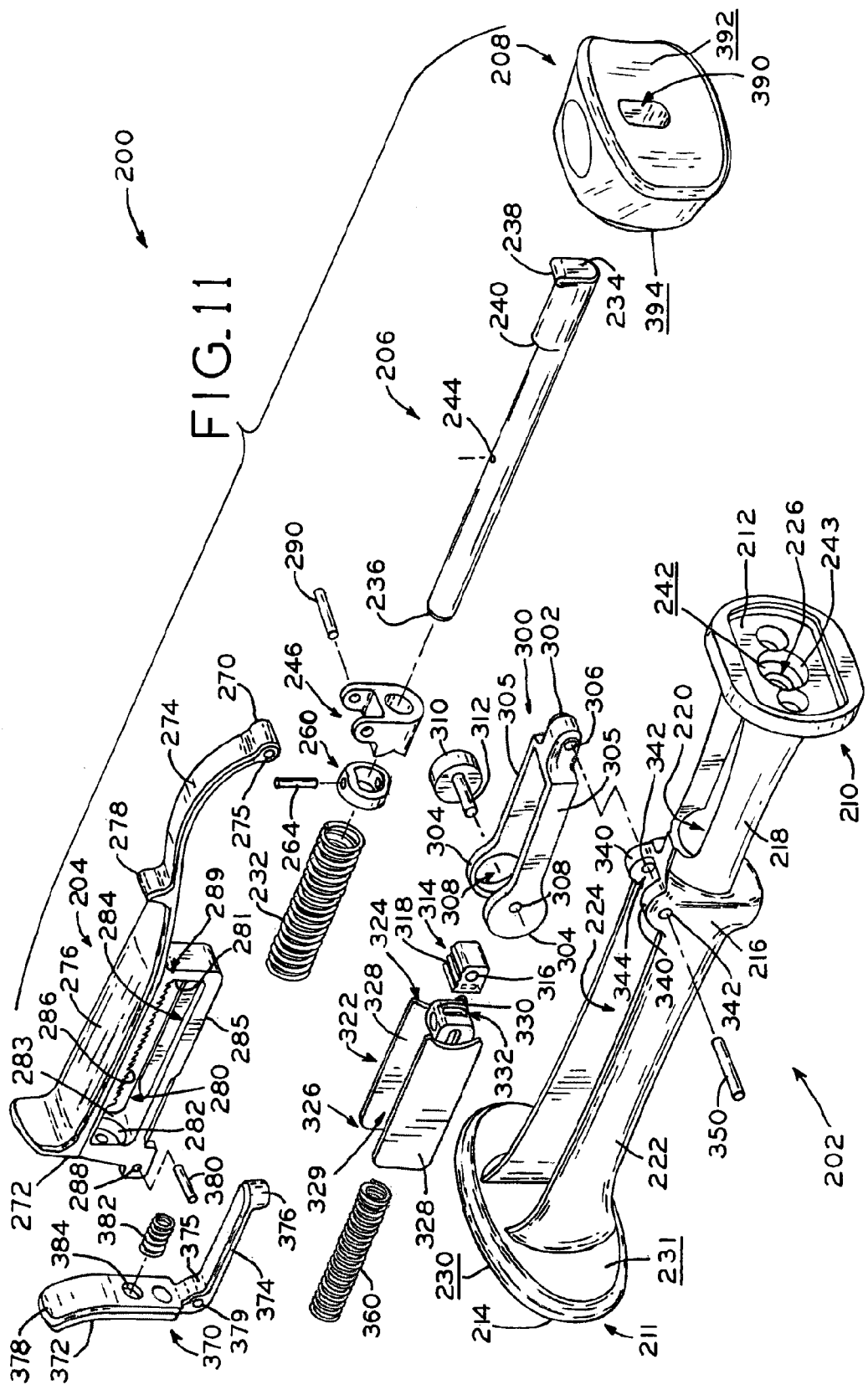
FIG. 11 is an exploded perspective view of a femoral component instrument in accordance with another exemplary embodiment of the present disclosure.
Figure 16A:
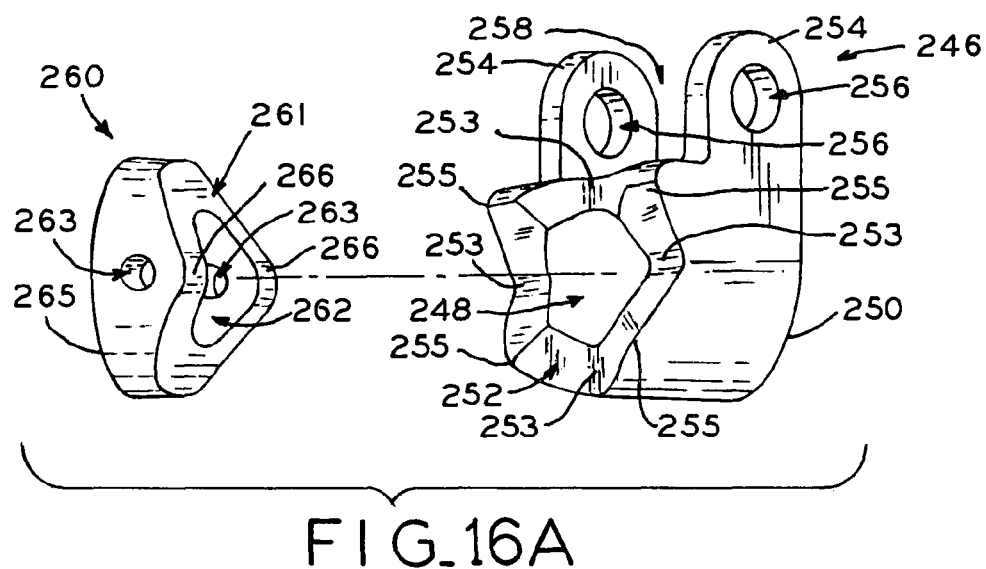
FIG. 16A is an exploded perspective view of a handle connection component and a bushing of the femoral component instrument of FIG. 11.
Figures 16B, 16C:
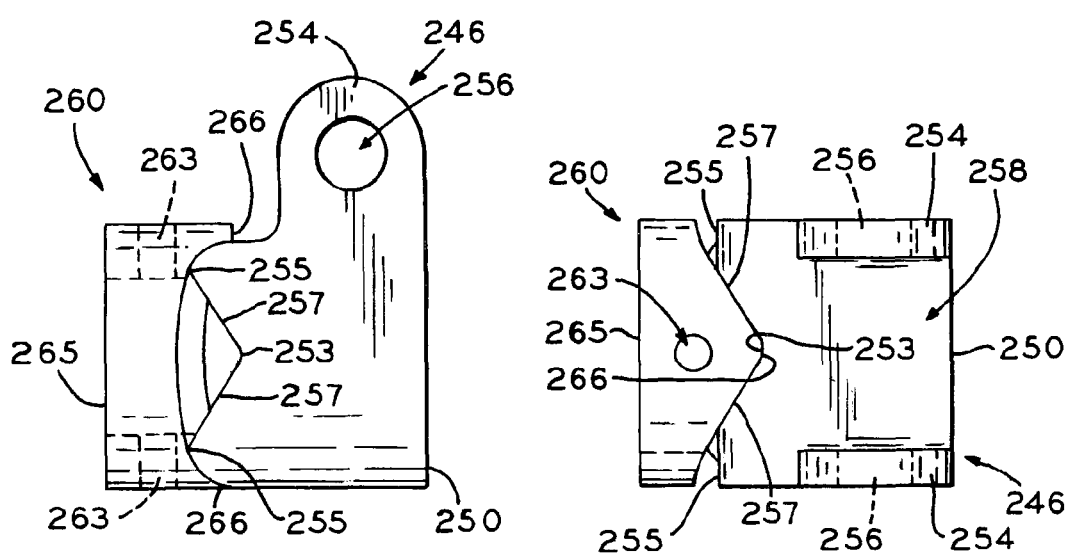
FIG. 16B is a side elevation view of the handle connection component and bushing of FIG. 16A.
FIG. 16C is an alternative side elevation view of the handle connection component and bushing of FIG. 16A.

For clarity, the details of handle connection component 246 and bushing 260 are only labeled in FIGS. 16A-16C although the details of handle connection component 246 and bushing 260 are also illustrated in FIG. 11. Referring to FIGS. 16A-16C, handle connection component 246 includes proximal wall 250, opposing distal wall 252, post receiving aperture 248 (FIG. 16A) spanning proximal wall 250 and distal wall 252, and side walls 254 each defining pin aperture 256. Distal wall 252 of handle connection component 246 includes four spaced apart indents 253 that may be, for example, substantially V-shaped indents. The four spaced apart indents include two pairs of opposing indents, each indent spaced 90° from one another. Between adjacent indents 253 are peaks 255. Each adjacent indent 253 and peak 255 are spanned by ramp 257 (FIGS. 16B and 16C). Distal wall 252 of handle connection component 246 includes indents 253 and peaks 255 spaced in an alternating manner along distal wall 252. Indents 253 and peaks 255 are each spaced along distal wall 252 and are each part of distal wall 252. Side walls 254 of handle connection component 246 also define handle extension receiving cavity 258 therebetween.

Referring to FIGS. 11 and 16A-16C, bushing 260 includes bushing proximal wall 261, opposing hushing distal wall 265, post receiving aperture 262 (FIG. 16A) spanning bushing proximal wall 261 and bushing distal wall 265, and pin receiving apertures 263. Bushing proximal wall 261 includes two opposing protrusions 266 sized and shaped to be received within corresponding indents 253 of distal wall 252 of handle connection component 246 as will be discussed in more detail below.

Referring to FIGS. 11 and 14, with proximal body spring 232 properly positioned within proximal body cavity 220, post distal end wall 236 is inserted through pad plate aperture 226. Once post distal end wall 236 extends into proximal body cavity 220, handle connection component 246 can be slid over post distal end wall 236 of post 206, i.e., post distal end wall 236 is inserted through post receiving aperture 248 (FIG. 16A) of handle connection component 246. Next, bushing 260 can be slid over post distal end wall 236 of post 206, i.e., post distal end wall 236 is inserted through post receiving aperture 262 (FIG. 16A) of bushing 260. With handle connection component 246 and bushing 260 positioned onto post 206, post distal end wall 236 can be slid through proximal body spring 232 and inserted through center body aperture 228 (FIG. 14) of center body portion 216 so that post distal end wall 236 extends into distal body cavity 224 as shown in FIG. 14. In this manner, the proximal end of proximal body spring 232 contacts bushing distal wall 265 (FIGS. 16A-16C). Next, bushing 260 can be positioned on post 206 such that pin receiving apertures 263 (FIGS. 16A-16C) of bushing 260 are aligned with pin aperture 244 of post 206, and then pin 264 can be inserted through pin receiving apertures 263 (FIGS. 16A-16C) of bushing 260 and pin aperture 244 of post 206 to secure bushing 260 to post 206. Bushing 260 is secured to post 206 such that rotation of post 206 rotates bushing 260. In alternative embodiments, bushing 260 may be welded to post 206. Handle connection component 246 is free to move up and down and rotate relative to post 206.

Referring to FIG. 16A, bushing proximal wall 261 and handle connection component distal wall 252 have mating features to secure locking lip 238 of post 206 in a particular position relative to pad plate 212. With post 206 connected to handle connection component 246 and bushing 260 as described above, post 206 is capable of rotational displacement about and within proximal body cavity 220. Locking lip 238 of post 206 can be rotated 90 degrees into one of four positions relative to pad plate 212. As discussed above, rotation of post 206, in turn, rotates bushing 260. Referring to FIGS. 11 and 16A-16C, proximal body spring 232 acts to bias bushing 260 into engagement with handle connection component 246. With bushing 260 in engagement with handle connection component 246, opposing protrusions 266 of bushing proximal wall 261 are disposed in corresponding opposing indents 253 of distal wall 252 of handle connection component 246 as shown in FIGS. 16B and 16C. In this manner, post 206 is secured in a particular position relative to pad plate 212.

When post 206 and, in turn, bushing 260 are rotated 90 degrees from one position to an adjacent position, opposing protrusions 266 of bushing proximal wall 261 are actuated to ride up respective opposing ramps 257 (FIGS. 16B and 16C) of distal wall 252 of handle connection component 246. Movement of protrusions 266 up respective opposing ramps 257 (FIGS. 16B and 16C) forces bushing 260 away from handle connection component 246 and compresses proximal body spring 232 until protrusions 266 move over respective peaks 255. Then proximal body spring 232 acts to bias bushing 260 back into engagement with handle connection component 246 and into the next pair of opposing indents 253 of distal wall 252 of handle connection component 246.

As previously discussed with the embodiment illustrated in FIGS. 1-10, when a femoral component is not provided for seating engagement to pad 208, pad 208 of femoral component instrument 200 may assist with rotation of post 206 to align post 206 to an appropriate securement position, i.e., one of the four positions that locking lip 238 of post 206 can be rotated to relative to instrument body 202, dependant on whether pad 208 is CR pad 158A (FIGS. 1, 6A, and 6B) or PS pad 158B (FIGS. 1, 7A, and 7B). Referring to FIGS. 11-14, proximal end wall 234 of post 206 is keyed to pad aperture 390 spanning femoral component contact surface 392 and instrument body contact surface 394 of pad 208. Specifically, pad aperture 390 is an elongate slot sized to accommodate locking lip 238 in the direction of elongation of pad aperture 390. Pad 208 of femoral component instrument 200 is keyed as described above in the embodiment illustrated in FIGS. 1-10 and the orientation of the keying features are dependent on the prosthesis type, i.e., a CR femoral component or a PS femoral component.

Referring to FIG. 11, handle assembly 204 includes handle proximal end 270, opposing handle distal end 272, handle bump 278 disposed between handle proximal end 270 and handle distal end 272, handle extension 274 extending from handle bump 278 to handle proximal end 270, handle extension pin aperture 275 located at handle proximal end 270, handle portion 276 extending from handle bump 278 to handle distal end 272, and handle receiving cavity 280. Handle assembly 204 also includes undercut surfaces 289 (only one of which can be seen in FIG. 11) beneath handle portion 276 on opposing sides of handle cavity 280. Handle cavity 280 includes handle cavity proximal wall 281, opposing handle cavity distal wall 283, counterbore 282 at handle cavity distal wall 283, longitudinal slot 284 formed through instrument body facing wall 285, and handle cavity teeth 286 located opposite instrument body facing wall 285. Handle assembly 204 also includes pin aperture 288 at handle distal end 272.

Referring to FIGS. 11-14 and 16A-16C, handle extension 274 is pivotally connected to handle connection component 246 by positioning handle extension pin aperture 275 within handle extension receiving cavity 258 of handle connection component 246 such that handle extension pin aperture 275 is aligned with respective pin apertures 256 of side walls 254. Once handle extension 274 is properly positioned relative to handle connection component 246, pin 290 is inserted through respective pin apertures 256 of handle connection component 246 and through handle extension pin aperture 275 of handle extension 274 to pin and pivotally connect handle extension 274 to handle connection component 246.

Referring to FIG. 11, link 300 includes proximal end 302, opposing distal end walls 304, opposing side walls 305, proximal pin aperture 306 at proximal end 302, and respective distal cam apertures 308 located at distal end walls 304. Referring to FIG. 11, cam 310 includes cam boss 312 extending eccentrically from cam 310. Again referring to FIG. 11, pawl 314 includes cam boss receiving aperture 316 therethrough, pawl teeth 318, and pawl protrusion 320 (FIGS. 14, 15A and 15B) located on a distal wall of pawl 314 facing pawl pusher 322. Referring to FIG. 11, pawl pusher 322 includes proximal end 324, opposing distal end 326, opposing side walls 328 extending from proximal end 324 to distal end 326 and defining spring receiving cavity 329 therebetween, and pawl pusher head component 330 located at proximal end 324 and including slot 332 for receiving pawl protrusion 320 (FIGS. 14, 15A and 15B) of pawl 314. In one embodiment, one side wall 328 of pawl pusher 322 can be removably attachable to pawl pusher head component 330.

Referring to FIGS. 11-14, proximal end 302 of link 300 is positioned between respective center body portion protruding walls 340 of center body portion 216 of instrument body 202 such that proximal pin aperture 306 of link 300 is aligned with respective pin apertures 342 of center body portion protruding walls 340. In this manner, proximal end 302 of link 300 is positioned in link receiving cavity 344 of center body portion 216 of instrument body 202. With proximal end 302 of link 300 properly positioned in link receiving cavity 344, pin 350 may be inserted through respective pin apertures 342 of center body portion protruding walls 340 and through proximal pin aperture 306 of link 300 to pivotally connect link 300 to center body portion 216 of instrument body 202.

After proximal end 302 of link 300 pivotally connected to center body portion 216 of instrument body 202, pawl 314 can be positioned inside handle cavity 280 of handle assembly 204. Next, opposing distal end walls 304 of link 300 can be positioned adjacent respective undercut surfaces 289 on opposing sides of handle cavity 280 and can be positioned relative to pawl 314 such that cam boss receiving aperture 316 of pawl 314 is aligned with respective distal cam apertures 308 of link 300. Next, cam boss 312 of cam 310 can be inserted into respective distal cam apertures 308 of link 300 and through cam boss receiving aperture 316 of pawl 314. In this manner, link 300 is pivotally connected to handle assembly 204 via cam 310 and pawl 314.

Figure 12:
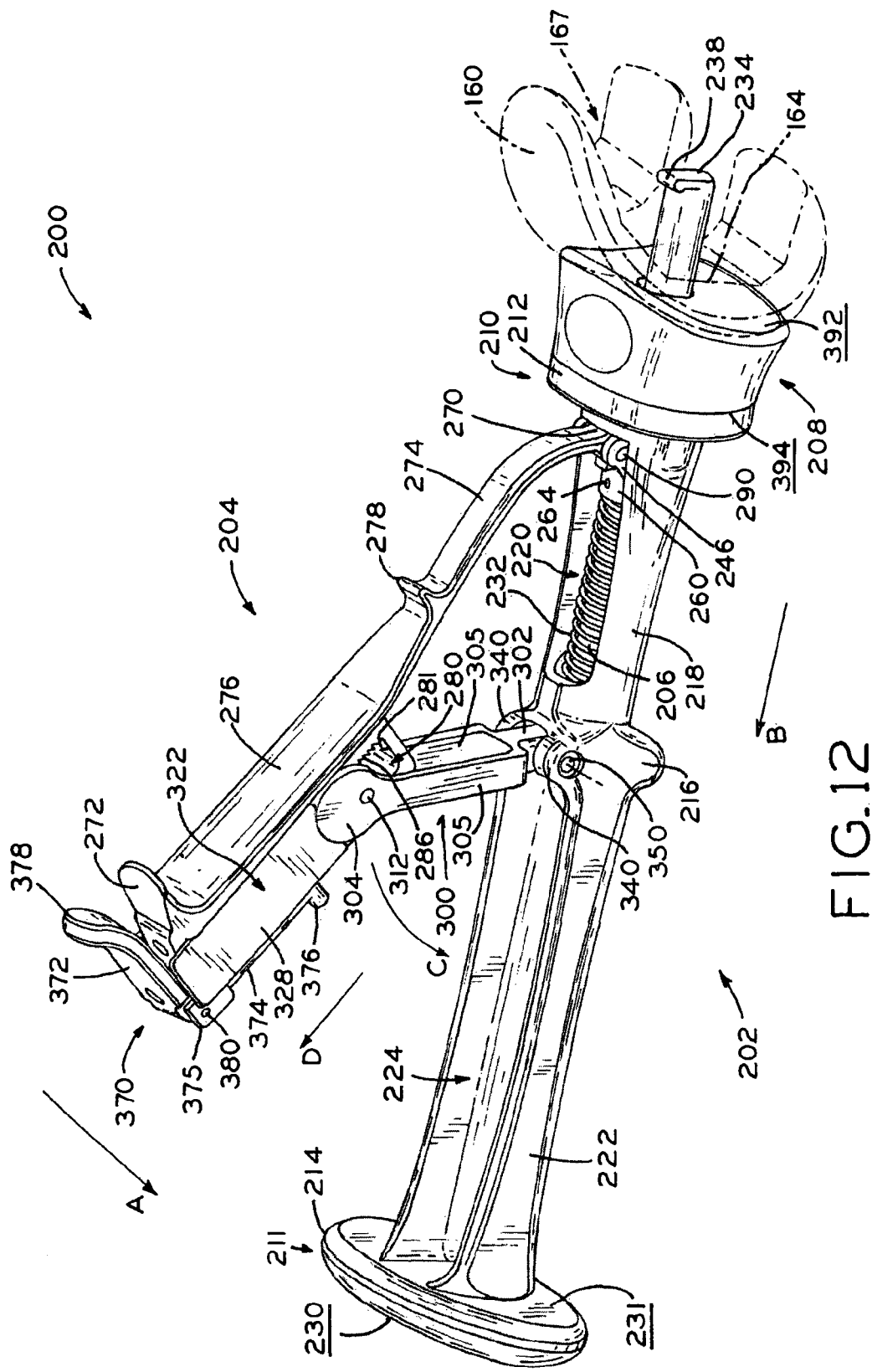
FIG. 12 is an assembled perspective view of the femoral component instrument of FIG. 11 in a fully open position.

Referring to FIGS. 11, 12 and 15A, with handle assembly 204 of femoral component instrument 200 in an open position as shown in FIG. 12, pawl 314 is actuated via link 300 and cam 310 to a position adjacent handle cavity proximal wall 281. In this position, pawl pusher 322 can be inserted into handle cavity 280 of handle assembly 204 by first inserting one side wall 328 of pawl pusher 322 into handle cavity 280 with the other side wall 328 of pawl pusher 322 oriented below instrument body facing wall 285 and thereafter rotating pawl pusher 322 into its final position with opposing side walls 328 of pawl pusher 322 located on opposing sides of handle cavity 280 adjacent respective undercut surfaces 289. With pawl pusher 322 disposed in its final position in handle cavity 280, pawl pusher head component 330 is positioned within handle cavity 280.

In alternative embodiments, pawl pusher 322 can be inserted into handle cavity 280 of handle assembly 204 by first removing one side wall 328 and then positioning pawl pusher head component 330 within handle cavity 280. Next, the removed side wall 328 can be reattached to pawl pusher head component 330 and pawl pusher 322 positioned within handle cavity 280 such that opposing side walls 328 of pawl pusher 322 are located on opposing sides of handle cavity 280 and pawl pusher head component 330 is positioned within handle cavity 280. Opposing side walls 328 of pawl pusher 322 are positioned adjacent respective undercut surfaces 289 on opposing sides of handle cavity 280.

With pawl pusher 322 properly positioned in handle cavity 280, pawl pusher 322 is slid along the longitudinal axis of handle cavity 280 towards handle cavity proximal wall 281 until pawl pusher 322 is connected to pawl 314 by positioning pawl protrusion 320 (FIGS. 14, 15A, and 15B) of pawl 314 in slot 332 (FIG. 11) of pawl pusher head component 330 as shown in FIGS. 14-15B. Next, handle cavity spring 360 is positioned in handle cavity 280 and in spring receiving cavity 329 (FIG. 11) of pawl pusher 322 such that a distal end of handle cavity spring 360 is disposed in counterbore 282 located in handle cavity distal wall 283 and a proximal end of handle cavity spring 360 contacts an interior portion of pawl pusher head component 330. In this manner, pawl pusher 322 is secured to handle assembly 204 so that pawl pusher 322 can axially move along the longitudinal axis of handle cavity 280, with movement of pawl pusher 322 towards handle cavity distal wall 283 compressing handle cavity spring 360. In alternative embodiments, handle cavity spring 360 is positioned on a rod (not shown) in handle cavity 280. The rod is used to provide stability to handle cavity spring 360 and guide movement of handle cavity spring 360 in handle cavity 280. In such an embodiment, pawl pusher 322 may not include opposing side walls 328.

With femoral component instrument 200 in the open position shown in FIG. 12, handle cavity spring 360 is expanded in its free state and forces pawl pusher 322 towards handle cavity proximal wall 281 (FIG. 15A). This causes pawl pusher 322 to force pawl 314 towards handle cavity proximal wall 281. With femoral component instrument 200 in the open position shown in FIG. 12, proximal body spring 232 and handle cavity spring 360 are each expanded in its free state, and locking lip 238 of post 206 is extended beyond femoral component contact surface 392 of pad 208 a maximum distance.

Referring to FIGS. 11, 13 and 14, unlocking component 370 includes arm 372, leg 374, middle portion 375 disposed between arm 372 and leg 374, instrument body contacting protrusion 376 extending from a proximal portion of leg 374, and tab 378 located at the end of arm 372 opposite middle portion 375. Middle portion 375 of unlocking component 370 defines pin aperture 379. With pin aperture 379 of unlocking component 370 positioned between and aligned with respective pin apertures 288 (only one of which is shown in the drawings) of handle distal end 272 of handle assembly 204, and with a distal end of unlocking component spring 382 positioned in counterbore 384 of arm 372 and a proximal end of unlocking component spring 382 positioned in counterbore 386 (FIGS. 14, 15A and 15B) of handle distal end 272 opposing counterbore 384 of arm 372, pin 380 can be inserted through respective pin apertures 288 of handle assembly 204 and through pin aperture 379 of unlocking component 370 to pin and pivotally connect unlocking component 370 to handle assembly 204.

Referring to FIGS. 11-16C, the use of femoral component instrument 200 to secure a femoral component such as femoral component 160 to pad 208 for placement, impaction and/or extraction of the femoral component will now be described. Referring to FIG. 12, with femoral component instrument 200 in the fully open position, and locking lip 238 of post 206 extended beyond femoral component contact surface 392 of pad 208 a maximum distance as discussed above, a user such as a surgeon positions a femoral component of a desired type and size, such as femoral component 160, on femoral component contact surface 392 of pad 208.

Referring to FIG. 12, with handle assembly 204 in a fully open position and proximal body spring 232 expanded in its free state, handle connection component 246 is pushed via bushing 260 against the distal surface of pad plate 212 in proximal body cavity 220. In this manner, with proximal body spring 232 expanded in its free state, handle assembly 204 is maintained in its open position and will not close until a force is exerted on handle assembly 204.

Handle assembly 204 pivots from the open position shown in FIG. 12 to the closed position shown in FIG. 13 via the pivot connection with handle connection component 246 and link 300. Referring to FIG. 12, with femoral component 160 properly positioned on femoral component contact surface 392 of pad 208 as shown in FIG. 12, a user begins to close handle assembly 204 by applying a force to handle portion 276 in a direction generally along arrow A (FIG. 12). Referring to FIG. 12, a user such as a surgeon can grip handle portion 276, to apply a force to handle assembly 204 in a direction generally along arrow A to close handle assembly 204, at a position adjacent handle bump 278. Handle bump 278 provides a stop which prevents the hand of a user from sliding when exerting a force on handle portion 276 thereby providing a secure grip.

As handle portion 276 of handle assembly 204 initially starts to be forced in the direction generally along arrow A (FIG. 12), handle extension 274 will begin to actuate handle connection component 246 in a direction generally along arrow B (FIG. 12). Actuation of handle connection component 246 in this manner will compress proximal body spring 232 via bushing 260 towards center body portion 216 of instrument body 202. As handle portion 276 of handle assembly 204 initially starts to be forced in the direction generally along arrow A (FIG. 12), proximal body spring 232 is compressed before handle cavity spring 360 disposed in handle cavity 280 because handle cavity spring 360 is stiffer than proximal body spring 232, i.e., handle cavity spring 360 has a higher spring constant than proximal body spring 232. Actuation of handle connection component 246 and compression of proximal body spring 232 in this manner, with bushing 260 pinned to post 206 as described above, will actuate locking lip 238 of post 206 in a direction generally along arrow B (FIG. 12) toward distal facet 164 of bone contacting surface 167 of femoral component 160. Actuation of handle connection component 246 and compression of proximal body spring 232 will continue until locking lip 238 of post 206 contacts distal facet 164 of bone contacting surface 167 of femoral component 160. Locking lip 238 cooperates with bone contacting surface 167 of femoral component 160 to secure femoral component 160 to femoral component instrument 200. As locking lip 238 engages distal facet 164 of femoral component 160, further actuation of handle assembly 204 as described below, supplies a locking force to femoral component 160 via locking lip 238. In this manner, a structural load or locking force is applied from locking lip 238 of post 206 onto femoral component 160 to secure femoral component 160 to pad 208 of femoral component instrument 200.

Referring to FIGS. 11, 12 and 15A, additional force exerted on handle portion 276 in a direction generally along arrow A (FIG. 12), to close handle assembly 204, will begin to compress handle cavity spring 360. The additional force exerted on handle portion 276 actuates or pivots link 300 in a direction generally along arrow C (FIG. 12) which, in turn, actuates pawl pusher 322 in a direction generally along arrow D (FIGS. 12 and 15A) thereby compressing handle cavity spring 360 toward handle cavity distal wall 283. Actuation of pawl pusher 322 in this manner results from the transfer of force through link 300, cam 310, and pawl 314 to pawl pusher 322 which, in turn, compresses handle cavity spring 360.

The amount of compression of handle cavity spring 360 is determined by the distance of locking lip 238 of post 206 from femoral component contact surface 392 of pad 208. The distance of locking lip 238 from femoral component contact surface 392 of pad 208 is determined by the thickness of distal facet 164 of femoral component 160. Handle cavity spring 360 is compressed more the farther locking lip 238 of post 206 is from femoral component contact surface 392 of pad 208 when locking lip 238 contacts distal facet 164 of femoral component 160.

Referring to FIGS. 11-15B, with continued force exerted on handle portion 276 in a direction generally along arrow A (FIG. 12) to continue closing handle assembly 204, handle cavity spring 360 is compressed in the manner described above until pawl teeth 318 of pawl 314 engage handle cavity teeth 286 as shown in FIGS. 14 and 15B via the cam connection between pawl 314 and cam 310 and the keyed connection between pawl 314 and pawl pusher 322 as will be described in more detail below. Engagement of pawl teeth 318 with handle cavity teeth 286 (disposed in handle cavity 280) prevents further compression of handle cavity spring 360. In one embodiment, femoral component instrument 200 is configured so that engagement of pawl teeth 318 of pawl 314 with handle cavity teeth 286 occurs when the longitudinal axis of handle cavity 280 is located approximately 15 degrees from the longitudinal axis of instrument body 202. At this point, pawl teeth 318 of pawl 314 will engage handle cavity teeth 286 as shown in FIGS. 14 and 15B. Pawl teeth 318 of pawl 314 engage handle cavity teeth 286 because the additional force exerted on handle portion 276 actuates or pivots link 300 in a direction generally along arrow C (FIG. 12) causing rotation of cam 310 relative to link 300 which, in turn, moves pawl 314 from the position shown in FIG. 15A to the position shown in FIG. 15B.

The additional force exerted on handle portion 276 in a direction generally along arrow A (FIG. 12) and compression of handle cavity spring 360 as described above, in turn, supplies additional locking force to femoral component 160 via locking lip 238. In this manner, an additional structural load or locking force is applied from handle assembly 204 to locking lip 238 of post 206 and onto femoral component 160 to further secure femoral component 160 to pad 208 of femoral component instrument 200.

FIGS. 14-15B illustrate cam boss 312 having a cylindrical shape, though it is contemplated that other shapes of cam boss 312 may be used. For example, cam boss 312 can have other multi-sided polygon cross-sectional shapes, such as square or rectangular cross-sectional shapes. Cam boss receiving aperture 316 of pawl 314 has a corresponding shape to receive cam boss 312. Referring to FIGS. 14-15B, pawl 314 is keyed to pawl pusher 322 via a mating connection between pawl protrusion 320 and slot 332 (FIG. 11) in pawl pusher head component 330. In this manner, the proximal wall of pawl pusher head component 330 is forced into engagement with the distal wall of pawl 314 by handle cavity spring 360 and the engagement between the proximal wall of pawl pusher head component 330 and the distal wall of pawl 314 guides movement of pawl 314 in a transverse direction relative to the longitudinal axis of instrument body 202 so that pawl 314 maintains proper alignment relative to handle cavity teeth 286 throughout the closing of handle assembly 204 as force exerted on handle portion 276 actuates link 300 in a direction generally along arrow C (FIG. 12) which, in turn, actuates the cam connection between pawl 314 and cam 310. In this manner, pawl teeth 318 properly engage handle cavity teeth 286 as shown in FIGS. 14 and 15B. In another embodiment, with cam boss 312 having a square cross-sectional shape and cam boss receiving aperture 316 of pawl 314 having a corresponding square cross-sectional shape, as link 300 is rotated in a direction generally along arrow C (FIG. 12) from the open position shown in FIG. 12 to the closed position shown in FIG. 13, pawl 314 rotates relative to link 300. In this manner, pawl 314 and link 300 never rotate independently from each other. Pawl 314 and link 300 rotate relative to one another so that pawl 314 and link 300 are always in the same orientation. This ensures that pawl teeth 318 properly engage handle cavity teeth 286 as shown in FIGS. 14 and 15B. In alternative embodiments, pawl 314 may not be keyed to pawl pusher 322.

With femoral component instrument 200 configured so that engagement of pawl teeth 318 of pawl 314 with handle cavity teeth 286 occurs when the longitudinal axis of handle cavity 280 is located approximately 15 degrees from the longitudinal axis of instrument body 202, additional force exerted on handle portion 276, in a direction generally along arrow A (FIG. 12) to move handle assembly 204 from a position approximately 15 degrees from the longitudinal axis of instrument body 202 to a fully closed position as shown in FIGS. 13 and 14, will apply force through and deform flexible handle extension 274 of handle assembly 204. This force applied to handle extension 274 will bend handle extension 274 as a force is exerted on handle portion 276 to close handle assembly 204. The additional force exerted on handle portion 276 will deform handle extension 274 before deforming link 300 because link 300 is a stiffer element than handle extension 274, i.e., link 300 is more resistant to elongation at the applied force. The stress generated from bending handle extension 274, i.e., curved handle extension 274 will straighten out so that a main axis of handle extension 274 will become approximately parallel to the longitudinal axis of instrument body 202, will apply approximately 150 pounds of structural load or force to femoral component 160 via locking lip 238 of post 206. The stress generated from bending handle extension 274 is applied to locking lip 238 of post 206 and onto femoral component 160 to further secure femoral component 160 to pad 208 of femoral component instrument 200.

The structural load or force applied to femoral component 160 via locking lip 238 of post 206 to secure femoral component 160 to pad 208 of femoral component instrument 200 is sufficient to hold and manipulate femoral component 160 during an orthopedic procedure. By utilizing the structural load created by femoral component instrument 200, femoral component instrument 200 is capable of securely holding femoral component 160 for a desired duration of time.

Handle extension 274 of an exemplary embodiment can be made of 455 stainless steel, 17-4 stainless steel, or other materials with similar mechanical and physical properties. The material of handle extension 274 is selected based on the modulus of elasticity of a material and the geometry of handle extension 274, i.e., shape, cross-section, and connection point locations.

In response to the force exerted on handle portion 276 in a direction generally along arrow A (FIG. 12) to move handle assembly 204 to a fully closed position as shown in FIGS. 13 and 14, an over-the-center locking occurs when link 300 pivots past its central longitudinal axis, i.e., over-center, as shown in FIGS. 13 and 14. In this position, the over-the-center locking locks handle assembly 204 within distal body cavity 224 of instrument body 202 in its closed position as shown in FIGS. 13 and 14.

Referring to FIGS. 13, 14 and 15B, to open handle assembly 204 from distal body cavity 224 of instrument body 202, tab 378 of unlocking component 370 needs only to be forcibly moved out of its closed position to unlock handle assembly 204. Unlocking component 370 is pivotally connected to handle assembly 204 via pin 380. In this manner, the force applied to tab 378 pivots leg 374 and instrument body contacting protrusion 376 of unlocking component 370 which contact instrument body facing wall 285 of handle assembly 204 to pry handle assembly 204 out of its closed position. In such a manner, exerting a force on tab 378 of unlocking component 370, with femoral component instrument 200 in a closed position as shown in FIG. 13, will flip handle assembly 204 and link 300 back over center, i.e., will overcome the over-the-center locking mechanism which locks handle assembly 204 to instrument body 202, and pivot handle assembly 204 open to the position shown in FIG. 12.

Femoral component instrument 200 may also act as an impactor without a femoral component positioned on pad 208 to limit travel of locking lip 238 of post 206. In this manner, locking lip 238 of post 206 is capable of movement from an external, exposed position proximal to femoral component contact surface 392 of pad 208 (FIG. 12) to an internal, retracted position distal to femoral component contact surface 392 of pad 208 and within pad aperture 390 (FIG. 14).

Without a femoral component positioned on pad 208 to limit travel of locking lip 238 of post 206, as handle portion 276 of handle assembly 204 initially starts to be forced in the direction generally along arrow A (FIG. 12), handle extension 274 will begin to actuate handle connection component 246 in a direction generally along arrow B (FIG. 12) which, in turn, compresses proximal body spring 232 via bushing 260 towards center body portion 216 of instrument body 202. As previously discussed, proximal body spring 232 is compressed before handle cavity spring 360 disposed in handle cavity 280 because handle cavity spring 360 is stiffer than proximal body spring 232. Actuation of handle connection component 246 and compression of proximal body spring 232 in this manner, with bushing 260 pinned to post 206 as described above, will actuate locking lip 238 of post 206 in a direction generally along arrow B (FIG. 12) until shoulder 240 of post 206 contacts proximal surface 242 of pad plate 212 as shown in FIG. 14. At this point, additional force exerted on handle portion 276 in a direction generally along arrow A (FIG. 12), to close handle assembly 204, will begin to compress handle cavity spring 360 as previously discussed.

Retraction of locking lip 238, as illustrated in FIG. 14, allows femoral component instrument 200 to be utilized as an impaction instrument to fully seat a femoral component to the distal end of a femur. With locking lip 238 retracted from femoral component contact surface 392 of pad 208, locking lip 238 of post 206 will not be adjacent to the prepared distal end of the femur and will not be available to interfere with the femoral component and the distal femur during impaction.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. An instrument for at least one of inserting, extracting, and impacting a selected one of a family of interchangeable distal femoral components comprising a first distal femoral component and a second distal femoral component, the instrument comprising:
   an instrument body;
   a post slidably coupled to the instrument body, the post slidable between a locked position and an unlocked position;
   a handle assembly pivotally connected to the post such that the handle assembly is rotatable between at least an open position and a closed position, the handle assembly defining a handle cavity and having a plurality of handle cavity teeth;
   a link having a proximal end and a distal end, the proximal end pivotally connected to the instrument body, the distal end coupled to a pawl slidably received within the handle cavity; and
   a handle cavity spring extending from a proximal end of the handle cavity and engaged to the pawl;
   wherein rotating the handle assembly toward the closed position causes the link to slide the pawl toward the proximal end of the handle cavity to initially slide the post toward the locked position into engagement with one of the family of interchangeable distal femoral components such that continued rotation of the handle assembly prior to engagement of the pawl compresses the handle cavity spring against the handle assembly;
   wherein the pawl is engagable to the handle cavity teeth to fix axial movement of the pawl within the handle cavity and pivotally connect the distal end of the link to the handle assembly such that further rotation of the handle assembly toward the closed position after engagement of the pawl to the handle cavity teeth pivots the link about the proximal end to further bias the post toward the locked position.

2. The instrument of claim 1, further comprising:
a proximal body spring extending between the instrument body and the post;
wherein sliding the post toward the locked position compresses the proximal body spring to bias the post toward the unlocked position.

3. The instrument of claim 1, wherein compressing the handle cavity spring biases the pawl toward a distal end of the handle cavity.

4. The instrument of claim 1, wherein the handle assembly is rotatable to an intermediate position;
wherein the intermediate position is between the open position and the closed position.

5. The instrument of claim 4, wherein the pawl engages the handle cavity teeth at the intermediate position such that the pawl is movable axially within the handle cavity as the handle is rotated between the open position and the closed position.

6. The instrument of claim 5, wherein the intermediate position is about 15 degrees from a longitudinal axis of the instrument body.

7. The instrument of claim 1, wherein the instrument body comprises:
a proximal surface having an opening therethrough, the proximal surface configured to contact a distal surface of the selected one of the first distal femoral component and the second distal femoral component when the selected one of the first distal femoral component and the second distal femoral component is seated with the instrument.

8. The instrument of claim 7, wherein the post comprises:
a locking end extendable through the opening in the proximal surface, the locking end having a locking lip extending transversely from the post, wherein the lip is positioned a first distance from the proximal surface in the locked position and positioned a second distance from the proximal surface in the unlocked position, the second distance being greater than the first distance;
when the post is in the unlocked position, the post is rotatable with respect to the handle from a first position to a second position, wherein, with the post maintaining the first position, the instrument is capable of cooperating with the first bone contacting surface configuration of the first distal femoral component to lock the first distal femoral component to the instrument and wherein, with the post maintaining the second position, the instrument is capable of cooperating with the second bone contacting surface configuration of the second distal femoral component to lock the second distal femoral component to the instrument.

9. The instrument of claim 8, wherein the first distal femoral component is a cruciate retaining femoral component, and the second distal femoral component is a posterior stabilized femoral component.

10. The instrument of claim 9, wherein the first position is rotated 90 degrees relative to the second position, and wherein when the selected femoral component is seated with the instrument, the locking end of the post extends through the proximal surface opening and the notch of the selected femoral component, such that when the post is in the first position, the post cooperates with the cruciate retaining femoral component such that the lip is alignable with the anterior end of the wall defining the notch of the cruciate retaining femoral component, and
when the post is in the second position, the post cooperates with the posterior stabilizing femoral component such that the lip is alignable with one of the medial and lateral ends of the wall defining the notch of the posterior stabilizing femoral component.

11. The instrument of claim 7, wherein the proximal surface of the instrument body is concave.

12. The instrument of claim 1, further comprising:
a base assembly including a bearing surface and an opposite surface, the bearing surface configured for receipt of a selected one of the first modular pad and the second modular pad, the base assembly including an opening extending from the bearing surface to the opposite surface, the opening positioned to align with the pad opening of the selected pad and the notch of the selected femoral component when the selected femoral component is seated against the selected pad and the base assembly receives the pad, the locking end of the post and the elongate pad opening of the first modular pad sized and shaped so that, with the first modular pad operably secured to the instrument, the locking end of the post is positioned with the locking lip in the first position and the locking lip is precluded from being positioned in the second position, and the locking end of the post and the elongate pad opening of the second modular pad sized and shaped so that, with the second modular pad operably secured to the instrument, the locking end of the post is positioned with the locking lip in the second position and the locking lip is precluded from being positioned in the first position.

13. The instrument of claim 12, wherein the base assembly includes an aperture configured to receive a corresponding peg extending distally from the distal surface of the selected one of the first pad and the second pad such that the base assembly receives the pad.

14. The instrument of claim 13, wherein the distal end of the instrument includes an aperture configured to proximally receive a barrel, the barrel including opposing pin apertures at a proximal end of the barrel and opposing pin apertures at a distal end of the barrel, the barrel including a plurality of elongated grooves extending at least partially from the proximal end of the barrel to the distal end of the barrel.

15. The instrument of claim 14, wherein the barrel further comprises:
a piston, including opposing piston pin apertures; received within the distal end of the barrel, the piston slidably coupled with the barrel by a piston pin received through opposing elongated grooves of the barrel and through the opposing piston pin apertures.

16. The instrument of claim 15, wherein the barrel further comprises a first spring received through the distal end of the barrel and abutting a distal end of the piston; and
a pin inserted in the opposing pin apertures at the distal end of the barrel such that a distal end of the first spring abuts the pin and the first spring is retained within the barrel.

* * * * *

UNITED STATES PATENT AND TRADEMARK OFFICE
CERTIFICATE OF CORRECTION

PATENT NO. : 9,901,462 B2
APPLICATION NO. : 14/943280
DATED : February 27, 2018
INVENTOR(S) : Jones et al.

Page 1 of 1

It is certified that error appears in the above-identified patent and that said Letters Patent is hereby corrected as shown below:

In the Claims

In Column 26, Line 52, in Claim 15, delete "apertures;" and insert --apertures,-- therefor Signed and Sealed this
Nineteenth Day of March, 2019

Andrei Iancu
*Director of the United States Patent and Trademark Office*